US012660996B2

(12) United States Patent
Yoshida et al.

(10) Patent No.: US 12,660,996 B2
(45) Date of Patent: Jun. 23, 2026

(54) ILLUMINATION CONTROL DEVICE, IMAGING DEVICE, ILLUMINATION CONTROL METHOD, AND PROGRAM

(71) Applicant: CASIO COMPUTER CO., LTD., Tokyo (JP)

(72) Inventors: Tohru Yoshida, Tokyo (JP); Katsuyuki Matsuo, Hanno (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 422 days.

(21) Appl. No.: 17/913,975

(22) PCT Filed: Feb. 12, 2021

(86) PCT No.: PCT/JP2021/005230
§ 371 (c)(1),
(2) Date: Sep. 23, 2022

(87) PCT Pub. No.: WO2021/192706
PCT Pub. Date: Sep. 30, 2021

(65) Prior Publication Data

US 2023/0118245 A1     Apr. 20, 2023

(30) Foreign Application Priority Data

Mar. 25, 2020     (JP) ................................. 2020-054891

(51) Int. Cl.
*A61B 1/06* (2006.01)
*A61B 1/303* (2006.01)
(Continued)

(52) U.S. Cl.
CPC .............. *A61B 1/0655* (2022.02); *A61B 1/06* (2013.01); *A61B 1/303* (2013.01); *G06V 10/141* (2022.01); *H04N 23/74* (2023.01)

(58) Field of Classification Search
None
See application file for complete search history.

(56) References Cited

U.S. PATENT DOCUMENTS

2002/0007123 A1*   1/2002   Balas ................... A61B 1/0646
                                                                    600/431
2009/0076368 A1*   3/2009   Balas ................. A61B 1/00149
                                                                    600/407
(Continued)

FOREIGN PATENT DOCUMENTS

JP          2017515588 A       6/2017

OTHER PUBLICATIONS

International Search Report (ISR) (and English language translation thereof) dated Apr. 20, 2021, issued in International Application No. PCT/JP2021/005230.
(Continued)

*Primary Examiner* — Anh Tuan T Nguyen
*Assistant Examiner* — Jae Woo
(74) *Attorney, Agent, or Firm* — Holtz, Holtz & Volek PC

(57) ABSTRACT

An illumination control device includes an image data acquirer, a control data acquirer, and a light source controller. The image data acquirer acquires target imaging-related data related to the target imaging in a case in which target imaging is performed in which an image of an inserter inserted into a hole part continuous with a target is captured by an imaging device together with the target. The control data acquirer acquires control data based on the acquired target imaging-related data. The light source controller controls an illumination state of a light source provided around an optical axis of the imaging device, based on the acquired control data.

8 Claims, 16 Drawing Sheets

(51) Int. Cl.
    *G06V 10/141*     (2022.01)
    *H04N 23/74*     (2023.01)

(56)           References Cited

U.S. PATENT DOCUMENTS

| | | | |
|---|---|---|---|
| 2014/0142433 A1 | 5/2014 | Greenstein et al. | |
| 2016/0073853 A1* | 3/2016 | Venkatesan | H04N 7/183 |
| | | | 348/68 |
| 2017/0049312 A1* | 2/2017 | Seth | A61B 1/303 |
| 2018/0344145 A1* | 12/2018 | Kozub | A61B 1/00194 |
| 2019/0356836 A1* | 11/2019 | Ida | G06T 5/92 |
| 2021/0161363 A1* | 6/2021 | Makino | G06N 3/084 |
| 2021/0289113 A1* | 9/2021 | Yeung | H04N 23/56 |
| 2021/0333094 A1* | 10/2021 | Wang | G01B 11/25 |
| 2022/0026276 A1* | 1/2022 | Harvill | G01J 3/528 |
| 2022/0239812 A1* | 7/2022 | Tokuchi | G06V 10/993 |
| 2023/0334695 A1* | 10/2023 | Tu | G06T 7/73 |
| 2024/0126495 A1* | 4/2024 | Kaku | G09G 5/14 |

OTHER PUBLICATIONS

Japanese Office Action (and English language translation thereof) dated Apr. 13, 2021, issued in counterpart Japanese Application No. 2020-054891.
Written Opinion dated Apr. 20, 2021, issued in International Application No. PCT/JP2021/00523.
Extended European Search Report (EESR) dated Aug. 8, 2023, issued in counterpart European Application No. 21776742.5.

* cited by examiner

FIG. 5A
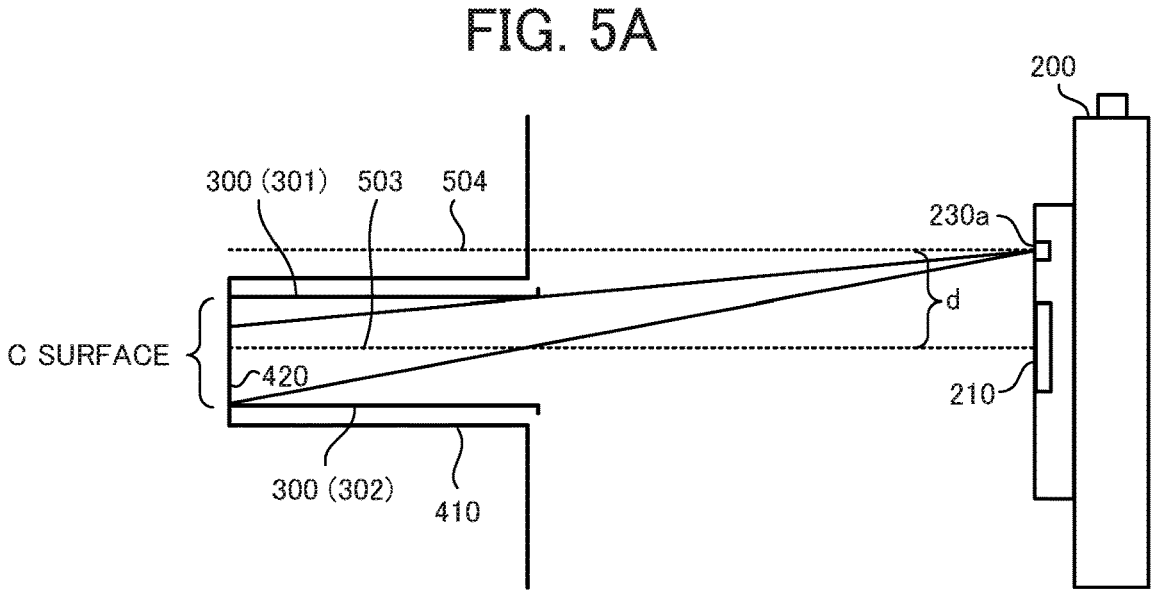
FIG. 5B
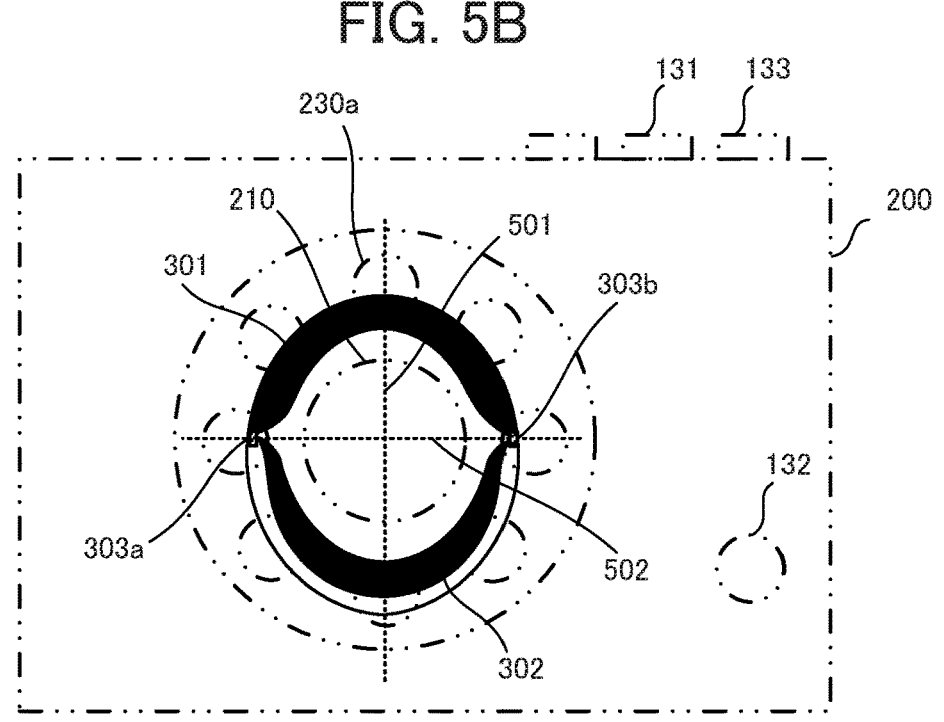
FIG. 5C

ILLUMINATION CONTROL DEVICE, IMAGING DEVICE, ILLUMINATION CONTROL METHOD, AND PROGRAM

TECHNICAL FIELD

The present disclosure relates to an illumination control device, an imaging device, an illumination control method, and a program.

BACKGROUND ART

A colposcopy camera has been developed as a device for capturing a cervix. For example, in a colposcopy camera disclosed in Patent Literature 1, a plurality of light sources (18) is arranged in a ring shape around an optical unit of the colposcopy camera, and four light beam emission units are arranged in a ring shape between these light sources and the optical unit. Furthermore, in the colposcopy camera in the related art, an image of the cervix captured by the colposcopy camera is analyzed for light spots generated by light emitted by these light beam emission units, information on the arrangement of the colposcopy camera with respect to the cervix is determined, and an instruction is provided to a user of the colposcopy camera based on the determined information, so that the arrangement of the colposcopy camera by the user is supported.

CITATION LIST

Patent Literature

Patent Literature 1: Unexamined Japanese Patent Publication No. 2017-515588

SUMMARY OF INVENTION

Technical Problem

In the colposcopy camera disclosed in Patent Literature 1, the user adjusts the position of the colposcopy camera based on the instruction provided from the colposcopy camera, so that the cervix is appropriately irradiated with light from the light source. However, conversely, in order to appropriately illuminate the cervix with the light from the light source, the user needs to adjust the position of the colposcopy camera based on the instruction.

The present disclosure has been made to solve the above problems, and an objective of the present disclosure is to provide an illumination control device, an imaging device, an illumination control method, and a program, capable of appropriately illuminating a target to be photographed even though a user adjusts no position.

Solution to Problem

In order to achieve the above objective, an illumination control device according to the present disclosure includes data acquisition means for acquiring target imaging-related data related to the target imaging, in a case in which target imaging is performed in which an image of an inserter inserted into a hole part continuous with a target is captured by an imaging device together with the target, control data acquisition means for acquiring control data based on the acquired target imaging-related data, and illumination control means for controlling an illumination state of a light source provided around an optical axis of the imaging device, based on the acquired control data.

Advantageous Effects of Invention

According to the present disclosure, a target to be photographed can be appropriately illuminated even though a user adjusts no position.

BRIEF DESCRIPTION OF DRAWINGS

FIG. 5A is a schematic diagram for explaining a state of light irradiation when the cervix is captured through the vaginal speculum by the imaging device according to Embodiment 1;

FIG. 5B is a view for explaining the orientation of the vaginal speculum when viewed from the entrance side of the vaginal speculum;

FIG. 5C is a view for explaining an example of a light illumination state on the surface of the cervix;

FIG. 13A is a diagram illustrating an example of the external appearance of the imaging device according to Embodiment 3;

FIG. 13B is a diagram for explaining an example of a prismer;

FIG. 13C is a cross-sectional view of the prismer taken along line A-A';

FIG. 13D is a cross-sectional view of the prismer taken along line C-C';

FIG. 13E is a cross-sectional view of the prismer taken along line E-E';

FIG. 13F is a cross-sectional view of the prismer taken along line G-G';

DESCRIPTION OF EMBODIMENTS

Figure 1:
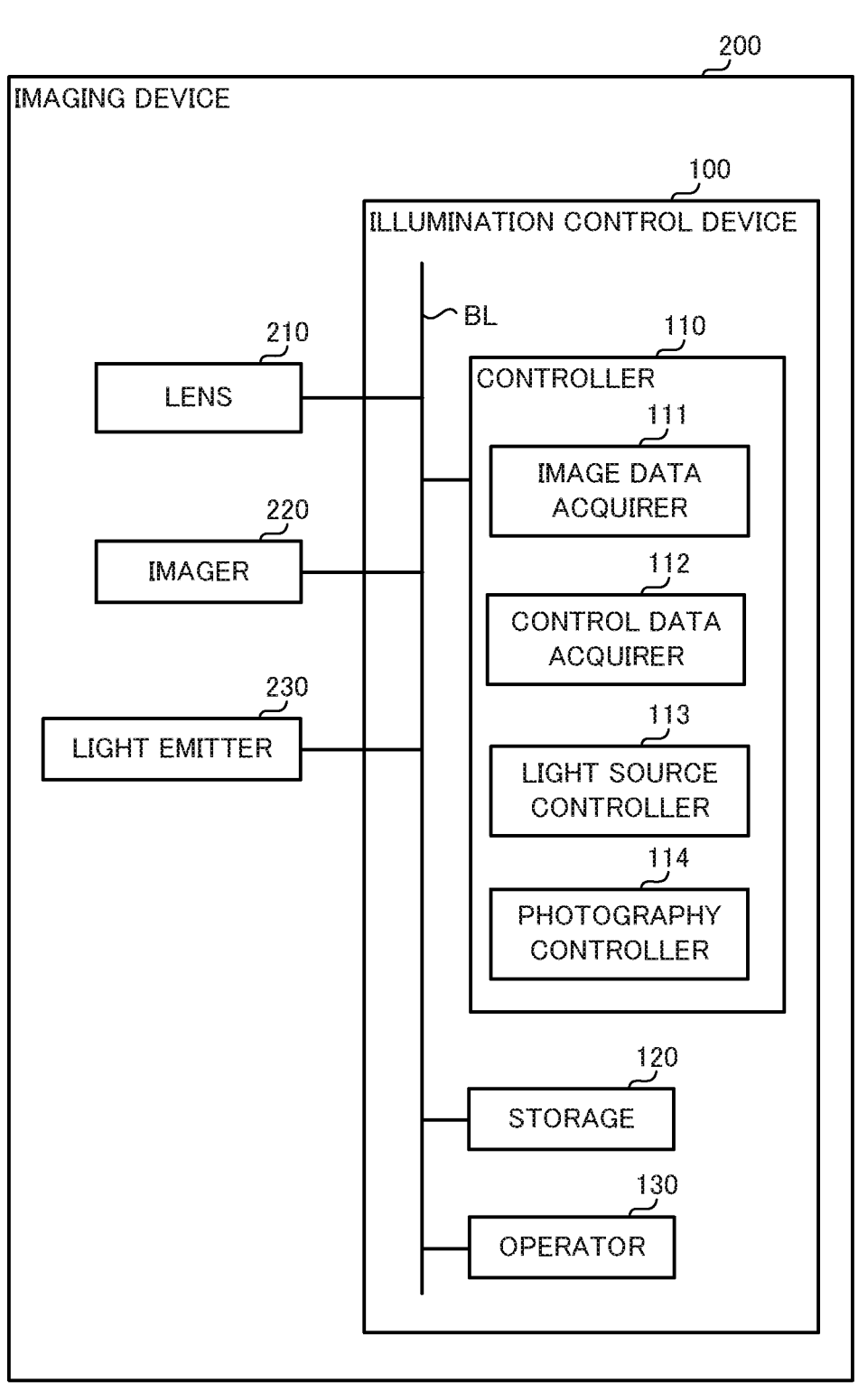
FIG. 1 is a diagram illustrating a functional configuration example of an imaging device according to Embodiment 1.

Hereinafter, embodiments of the present disclosure are described with reference to the drawings. In each drawing, the same or corresponding parts are denoted by the same reference numerals.

Embodiment 1

An imaging device 200 according to Embodiment 1 is a device for photographing a cervix at the back of a human vagina as, for example, a target to be photographed, and is a so-called colposcopy camera. As illustrated in FIG. 1, the imaging device 200 includes a lens 210, an imager 220, a light emitter 230, and an illumination control device 100. The imaging device 200 photographs the cervix by irradiating the cervix with light from the light emitter 230 selected by the illumination control device 100 and capturing an image of light, which is reflected by the cervix and passes through the lens 210, by the imager 220.

Figure 2:
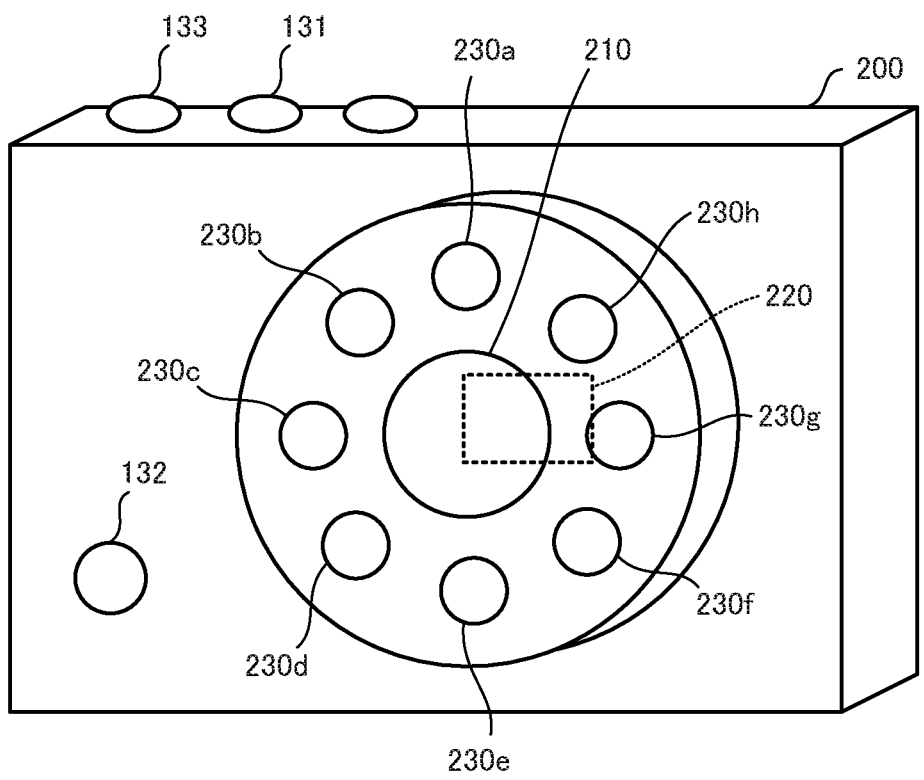
FIG. 2 is a diagram illustrating an example of the external appearance of the imaging device according to Embodiment 1.

Furthermore, as illustrated in FIG. 2, in appearance, the imaging device 200 includes a plurality of light emitters 230 (for example, eight light emitters 230a to 230h as illustrated in FIG. 2) as light sources around an optical axis of the imaging device 200 (optical axis of the lens 210). Furthermore, the imaging device 200 includes a light emitting release button 131, a focus key 132, and a shutter key 133 as an operator 130. Usually, in the imaging device 200, when a side where the light emitting release button 131 exists is set to up, since capturing is performed on a target to be photographed toward the lens 210, the direction of the light emitter 230a is set to up, the direction of the light emitter 230c is set to right, the direction of the light emitter 230e is set to down, and the direction of the light emitter 230g is set to left when viewed from the center of the lens 210 for convenience.

When a user presses the light emitting release button 131, light irradiation by the light emitter 230 is canceled. Furthermore, the focus key 132 sets the search direction of a focus distance (distance to a subject to be focused) when focusing the lens in the opposite direction to the ordinary one. For lens focus adjustment, the distance to the subject to be focused from infinity toward a short distance is usually searched. However, when the focus key 132 is pressed, the distance (focus distance) to the subject to be focused from a short distance toward infinity is searched. The focusing method is arbitrary, but for example, a phase difference autofocus (AF) method or a contrast AF method is used. The focus key 132 is also used as a trigger to start an illumination control process to be described below. Furthermore, when the user presses the shutter key 133, the imager 220 performs imaging.

Figure 18:
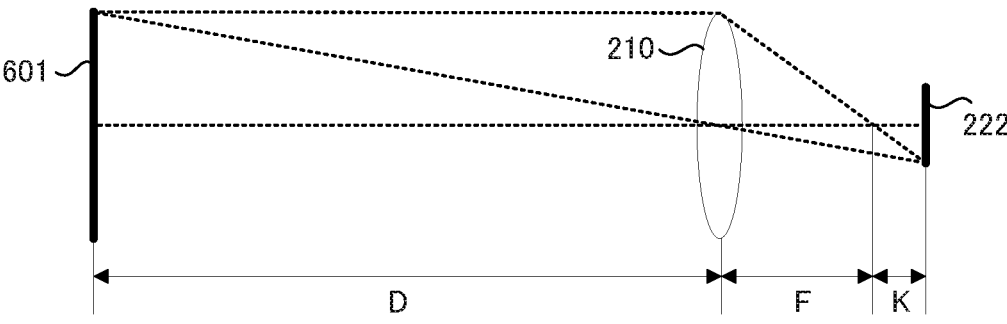
FIG. 18 is a diagram for explaining a method for measuring a distance to a subject.

The lens 210 collects light from the cervix on an imaging element 222 included in the imager 220. As illustrated in FIG. 18, the lens 210 has a function of adjusting a focal length F and an extension amount K of the lens so that light from a subject 601 is focused on the imaging element 222. Based on an image formation formula of the lens, the relationship of the following equation (1) is established between a focus distance D from the lens 210 to the subject 601 and a focal length F and the extension amount K of the lens 210.

$$1/D + 1/(F+K) = 1/F \tag{1}$$

Accordingly, the focus distance D can be obtained by, for example, the following equation (2).

$$D = F(F+K)/K \tag{2}$$

The imager 220 includes, for example, an imaging element such as a charge coupled device (CCD) image sensor and a complementary metal oxide semiconductor (CMOS) image sensor, and captures an image by converting light passing through the lens 210 into an electric signal.

The light emitter 230 includes a plurality of light emitting elements such as light emitting diodes (LEDs) around the optical axis of the lens 210, and irradiates a target to be photographed with light. The light emitter 230 serves as a light source.

The illumination control device 100 includes a controller 110, a storage 120, and the operator 130 as illustrated in FIG. 1.

The controller 110 includes a central processing unit (CPU) and the like, and controls the illumination control device 100 and the imaging device 200 by executing a program stored in the storage 120.

The storage 120 includes a read only memory (ROM), a random access memory (RAM), and the like, and stores a program to be executed by the CPU of the controller 110, necessary data, and the like.

The operator 130 is a user interface such as a push button switch, and receives operation input from the user. The illumination control device 100 includes, for example, the light emitting release button 131 and the focus key 132 illustrated in FIG. 2 as the operator 130.

Figure 3:
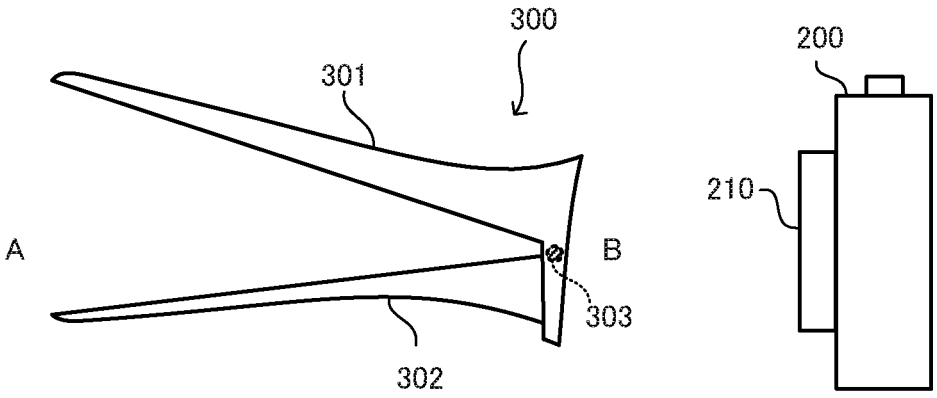
FIG. 3 is a diagram illustrating an example of the external appearance of a vaginal speculum according to Embodiment 1 and for explaining the positional relationship between the vaginal speculum and the imaging device at the time of imaging.

When photographing the cervix by the imaging device 200, the user inserts a vaginal speculum 300 illustrated in FIG. 3 into a vagina from a distal end side (side A illustrated in FIG. 3), and photographs the cervix through the vaginal speculum 300 from an entrance side of the vaginal speculum 300 (side B illustrated in FIG. 3). The vaginal speculum 300 is divided into an upper part 301 and a lower part 302, has the distal end side openable and closable with a main part 303 as a fulcrum, has a substantially tubular shape when inserted into the vagina, and protrudes from the vagina. Furthermore, the vaginal speculum 300 expands the vagina by opening the distal end sides of the upper part 301 and the lower part 302 with a screw (not illustrated) while being inserted into the vagina. The user can observe the cervix at the back of the vagina from the entrance side of the vaginal speculum 300 (opposite to the distal end sides of the upper part 301 and lower part 302) through a space between the upper part 301 and the lower part 302.

Figure 4A:
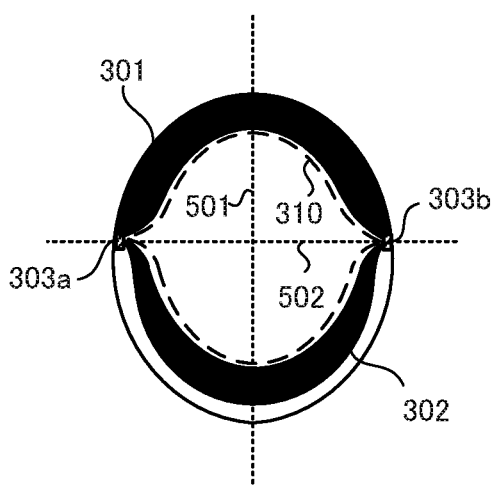
FIG. 4A is a view of the vaginal speculum when viewed from an entrance side.
Figure 4B:
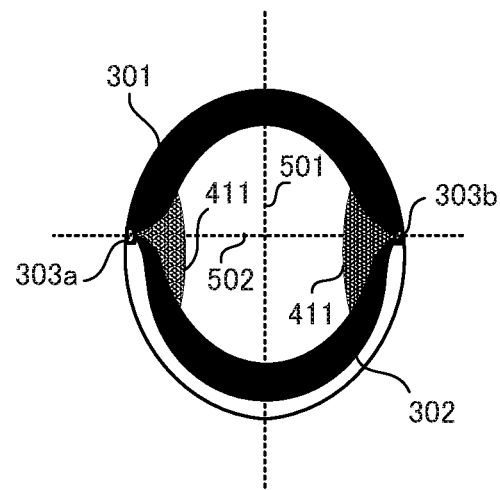
FIG. 4B is a view for explaining a state where a thick wall of vagina is protruding.

When the vaginal speculum 300 is viewed from the entrance side of the vaginal speculum 300 (opposite to the vagina) in the insertion direction into the vagina (hereinafter, referred to as "vaginal speculum insertion direction"), there are convex portions in the vicinity of main parts 303$a$ and 303$b$ as illustrated in FIG. 4A, but (when the direction in which the upper part 301 exists is set to up, the direction in which the lower part 302 exists is set to down, the direction in which the main part 303$a$ exists is set to left, and the direction in which the main part 303$b$ exists is set to right) the left and right are generally slightly crushed. Furthermore, a cross section 310 (hereinafter, for convenience, referred to as "cross section 310 of the vaginal speculum 300") of the vaginal speculum 300 orthogonal to the vaginal speculum insertion direction has a shape having an elliptical shape (hereinafter, referred to as "elliptical shape"). However, the elliptical shape is not limited to a mathematically defined ellipse (accordingly, the elliptical shape is also called a substantially elliptical shape). For example, a shape close to an ellipse as illustrated in FIG. 4A is also included in the elliptical shape. Furthermore, in a state where the vaginal speculum 300 is inserted into the vagina, since a thick wall 411 of the vagina protrudes toward a part, where the vaginal speculum 300 does not exist, between the upper part 301 and the lower part 302 of the vaginal speculum 300 as illustrated in FIG. 4B, the cervix is more widely observed in the direction in which a major axis 501 of the cross section of the speculum 300 extends than in the direction in which a minor axis 502 extends. In FIG. 4A and FIG. 4B, and FIG. 5B, FIG. 6B, and FIG. 8 to be described below, the major axis 501 and the minor axis 502 are drawn longer than the cross section of the vaginal speculum 300 for convenience.

When the user photographs the cervix through the vaginal speculum 300, since the cervix is located at the back of the vagina, the cervix needs to be irradiated with light from the light emitter 230 through the vaginal speculum 300 having a substantially elliptical cross section. However, since the light emitter 230 is provided around the optical axis of the imaging device 200, some deviation exists between the optical axis of the light emitter 230 and the optical axis of the lens 210. Therefore, it is difficult to properly irradiate the entire cervix with the light from the light emitter 230 while accommodating the cervix in the angle of view of the imaging device 200.

For example, as illustrated in FIG. 5A, a case where a cervix 420 is irradiated with light from the light emitter 230$a$ at the uppermost portion of the imaging device 200 through the vaginal speculum 300 inserted into a vagina 410 is considered. As illustrated in FIG. 5A and FIG. 5B in which the imaging device 200 is overlapped with the vaginal speculum 300 by a two dot chain line, in a case where the major axis 501 of the vaginal speculum 300 matches a straight line connecting the optical axis of the imaging device (lens 210) and the optical axis of the light emitter 230$a$ when viewed from the vaginal speculum insertion direction (or direction in which the optical axis of the imaging device 200 extends), the surface (C surface) of the cervix 420 has a region 511 where the light from the light emitter 230$a$ reaches and a shadow region 512 (vignetting) where no light reaches as illustrated in FIG. 5C.

Figure 6A:
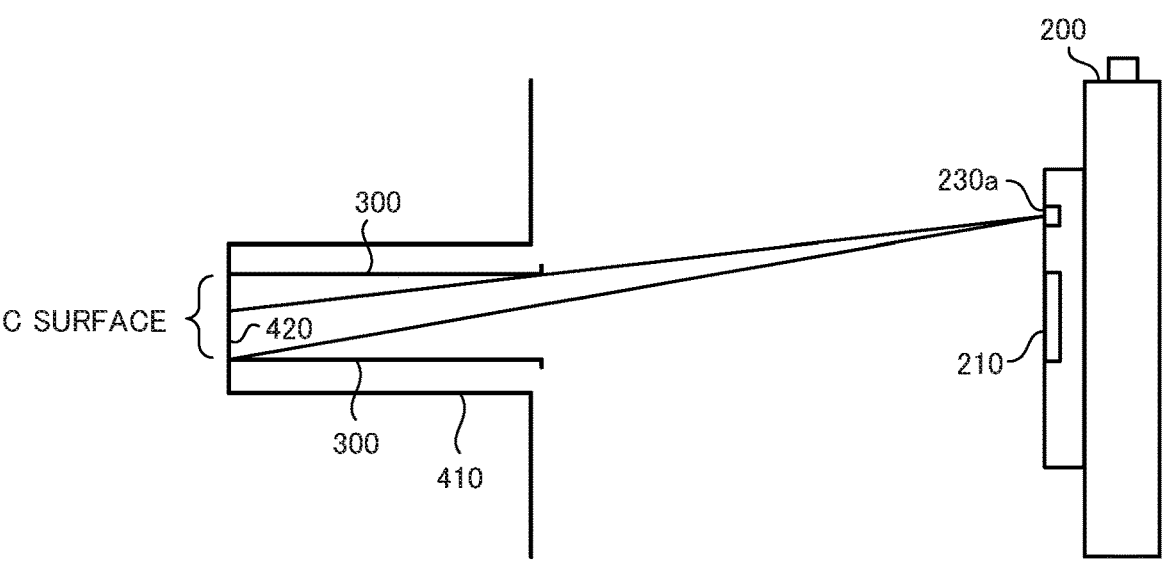
FIG. 6A is a diagram for explaining a light illumination state when the cervix is captured through the vaginal speculum by the imaging device according to Embodiment 1 in a state where the vaginal speculum is rotated 90° with respect to the orientation of the vaginal speculum in FIG. 5B.
Figure 6B:
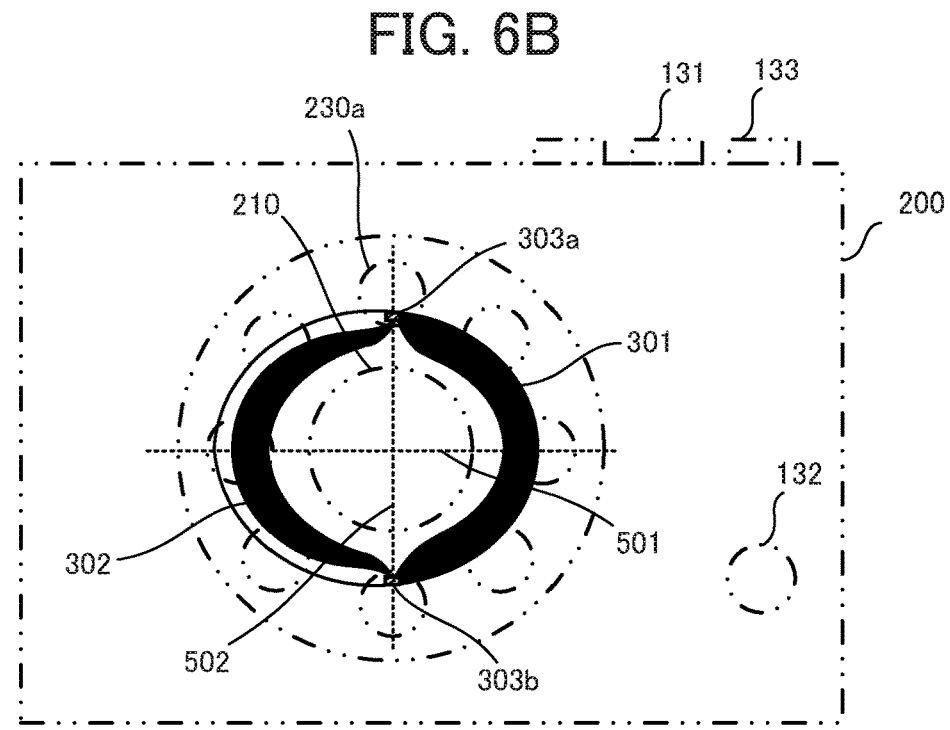
FIG. 6B is a view for explaining the orientation of the vaginal speculum rotated 90° with respect to the orientation of the vaginal speculum in FIG. 5B when viewed from the entrance side of the vaginal speculum.
Figure 6C:
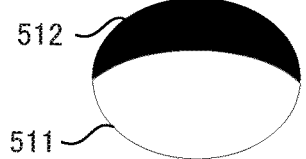
FIG. 6C is a view for explaining an example of a light illumination state on the surface of the cervix when the vaginal speculum is rotated 90° with respect to the orientation of the vaginal speculum in FIG. 5B.

An area of the area 511 where the light reaches and an area 512 of the shadow change depending on the orientation (angle) of the vaginal speculum 300. For example, as illustrated in FIG. 6B, in a case where the vaginal speculum 300 is rotated 90° from the state of FIG. 5B around an axis extending from the center of the cross section of the vaginal speculum 300 in the vaginal speculum insertion direction and the minor axis 502 of the vaginal speculum 300 is allowed to match the straight line connecting the optical axis of the imaging device 200 and the optical axis of the light emitter 230$a$ when viewed from the vaginal speculum insertion direction, a region 511 on the surface (C surface) of the cervix 420, where the light from the light emitter 230$a$ reaches, is smaller than the region 511 illustrated in FIG. 5C, as illustrated in FIG. 6A and FIG. 6C. Furthermore, in such a case, a shadow region 512 (vignetting), where no light reaches, is smaller than the shadow region 512 illustrated in FIG. 5C.

As is clear by compared to the C surfaces of FIG. 5A and FIG. 6A, when the orientation of the vaginal speculum 300 is orientation between the orientation of FIG. 5B and the orientation of FIG. 6B, an area of the area 511 where light reaches is an area between the area of the area 511 illustrated in FIG. 5C and the area of the area 511 illustrated in FIG. 6C.

Furthermore, as is clear from FIG. 5A, the smaller the shortest distance d between a line extending from the center of the cross section 310 of the vaginal speculum 300 in the vaginal speculum insertion direction (hereinafter, referred to as "vaginal speculum cross section center line" and line matching an optical axis 503 of the lens 210 in FIG. 5A) and an optical axis 504 of the light emitter 230$a$, the larger the area of the region 511 where light from the light emitter 230$a$ reaches the cervix 420.

Accordingly, in order to increase the area of the region 511 where light reaches as much as possible, the controller 110 may select a light emitter 230 in which the angle of the major axis 501 of the cross section of the vaginal speculum 300 with respect to a straight line connecting the optical axis of the imaging device 200 and the optical axis of a light emitter 230 to emit light is as small as possible and the distance between the center of the cross section 310 of the vaginal speculum 300 and the optical axis of the light emitter 230 is as small as possible, and turn on the selected light emitter 230. The center of the cross section 310 of the vaginal speculum 300 can be considered to be a middle point of the two main parts 303$a$ and 303$b$ of the vaginal speculum 300 for convenience.

In view of the relationship between the angle and the center of the cross section of the vaginal speculum 300 and the shadow region 512 as described above, the controller 110 selects a light emitter capable of appropriately illuminating the cervix 420 from the plurality of light emitters 230$a$ to 230$h$, thereby controlling the illumination state by the light emitter 230 so that the cervix 420 can be appropriately illuminated. In such a case, the controller 110 serves as an image data acquirer 111, a control data acquirer 112, a light source controller 113, and a photography controller 114 illustrated in FIG. 1 by executing the program stored in the storage 120.

The image data acquirer 111 acquires the electrical signal output by the imager 220 as image data of the image captured by the imager 220. For example, when an image of the vaginal speculum 300 inserted into the vagina continuous with the cervix 420 is captured by the imager 220 together with the cervix 420, the image data acquirer 111 acquires the image data of the image captured by the imager 220 as data related to this imaging (target imaging) (target imaging-related data) The image data acquirer 111 serves as data acquisition means.

The control data acquirer 112 acquires a position parameter representing the positional relationship between the light emitter 230 and the vaginal speculum 300 as control data used for controlling an illumination state by the light emitter 230, based on the image data (target imaging-related data) acquired by the image data acquirer 111. More specifically, the control data acquirer 112 acquires feature points $\alpha$ and $\beta$ having the above-mentioned elliptical shape from the image data by an illumination control process to be described below, and acquires the positional relationship (coordinates (xc, yc) of a middle point O of the feature points $\alpha$ and $\beta$) between an angle $\theta$ of a major axis of the elliptical shape (the cross section of the vaginal speculum 300 to be described below) with respect to a y-axis (base line extending in the direction orthogonal to the optical axis of the lens 210) to be described below and the center of the elliptical shape with the optical axis of the lens 210 in the image data as a reference from the acquired feature points $\alpha$ and $\beta$ as the position parameter. The control data acquirer 112 serves as control data acquisition means. The base line extending in the direction orthogonal to the optical axis of the lens 210 when acquiring the angle $\theta$ of the position parameter is not limited to the y-axis and may be an x-axis. Furthermore, the angle $\theta$ of the position parameter is not limited to the angle of the major axis of the elliptical shape with respect to the base line, and may be an angle of a minor axis of the elliptical shape with respect to the base line.

The light source controller 113 controls the illumination state of the plurality of light emitters 230 (230_a_ to 230_h_) (light sources) of the imaging device 200 based on the control data (position parameter) acquired by the control data acquirer 112. For example, the light source controller 113 considers the relationship between the angle and the center of the cross section of the vaginal speculum 300 and the shadow region 512 described with reference to FIG. 4A to FIG. 6C, and controls the illumination states of the light emitters 230 based on the control data according to a control rule constructed based on the relationship between the control data and the illumination states of the light emitters 230. Specifically, the light source controller 113 selects a light emitter 230 (light emitting part 230 capable of irradiating the widest range of the cervix with light) for illuminating the cervix from the plurality of light emitters 230_a_ to 230_h_ based on the position parameter, and causes the selected light emitter 230 to emit light. The light source controller 113 functions as illumination control means for controlling the illumination state of the light emitter 230.

The photography controller 114 causes the imager 220 to photograph a target to be photographed in a state where the light source controller 113 controls the illumination states of the plurality of light emitters 230 (230_a_ to 230_h_) (light sources). The photography controller 114 serves as capturing control means.

Next, the illumination control process performed by the controller 110 is described with reference to FIG. 7. This process is a process for controlling the light emitting state of the light emitter 230, and is started when an instruction to start the illumination control process is received from the user via the operator 130. For example, when the user turns on the focus key 132, the illumination control process is started.

First, the image data acquirer 111 changes the focal length or the extension amount of the lens 210 in order to find a focus distance that is in focus from the closest distance toward infinity, and searches for a focus distance to be focused first (step S101).

Next, the image data acquirer 111 acquires image data of a captured image (live view image) captured by the imager 220 through the focused lens 210 (step S102). The captured image is an image obtained by capturing the vaginal speculum 300 inserted into the vagina 410 continuous with the cervix 420 together with the cervix 420. Step S102 is also referred to as an image data acquisition step.

Then, the control data acquirer 112 extracts the feature points $\alpha$ and $\beta$ by analyzing the acquired image data (step S103). Hereinafter, the feature points $\alpha$ and $\beta$ are described. By searching for a focus distance to be focused from a close distance toward the imaging device 200 at the vaginal speculum 300, and capturing an initially focused image, the image data acquirer 111 acquires the image data as illustrated in FIG. 4A. In the cross section 310 of the vaginal speculum 300 in the image data, since the vicinity of the main parts 303_a_ and 303_b_ of the vaginal speculum 300 has a large difference from a true ellipse and is a peculiar part having a characteristic on an image basis, the vicinity is easily extracted as a feature point through image analysis. Therefore, the control data acquirer 112 extracts the main part 303_a_ as the feature point $\alpha$ and the main part 303_b_ as the feature point $\beta$.

Figure 8:
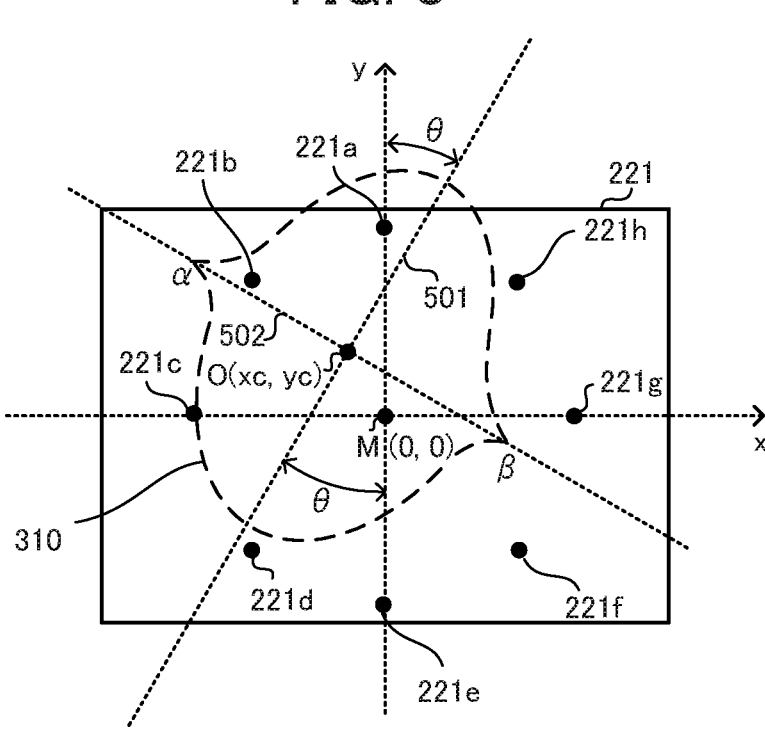
FIG. 8 is a diagram for explaining the calculation of coordinates of a middle point and an angle of a long axis of an elliptical shape.
Figure 9:
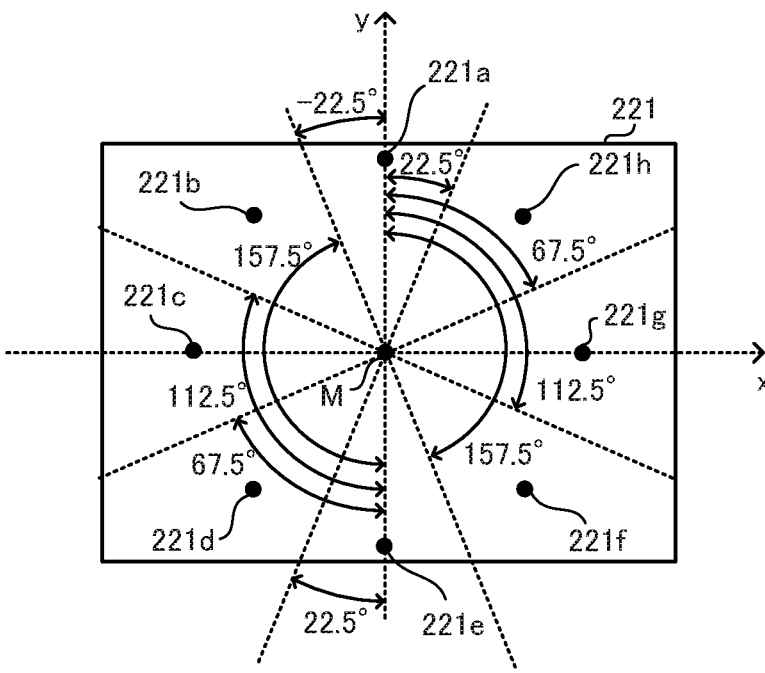
FIG. 9 is a diagram for explaining the selection of a target illumination light source.

Returning to FIG. 7, the control data acquirer 112 then calculates the coordinates (center coordinates) of the center of the cross section 310 of the vaginal speculum 300 in the captured image acquired in step S102 from the positions of the feature points $\alpha$ and $\beta$ (Step S104). As illustrated in FIG. 8, a coordinate system that defines the center coordinates is defined as follows according to the angle of view included in the imager 220. However, while FIG. 5B and FIG. 6B are views in the direction in which the vaginal speculum 300 is viewed from the imaging device 200, FIG. 8 and FIG. 9 are diagrams in the direction in which the imaging device 200 is viewed from the vaginal speculum 300.

First, the horizontal direction of the angle of view 221 of the imaging device 200 is defined as an x direction, the vertical direction of the angle of view 221 is defined as a y direction, and in the angle of view 221, an x-axis and a y-axis are defined to pass through the center of the angle of view 221. When there are X pixels in the horizontal direction, x Y pixels in the vertical direction at the angle of view 221, first, the uppermost left coordinates at the angle of view 221 are defined as (1, 1), and the lowermost right coordinates are defined as (X, Y), the x-coordinate of the center M is defined as X/2 (however, X/2+0.5 when X is odd), and the y-coordinate of the center M is defined as Y/2 (however, Y/2+0.5 when Y is odd) in correspondence to the number of pixels. Next, the x-axis and the y-axis are defined so that the coordinates of the center M are (0, 0). For example, when the number of pixels of the imaging element is 640 in the horizontal direction x and 480 in the vertical direction y, the uppermost left coordinates are defined as (−319, −239), the lowermost right coordinate is defined as (320, 240), and the coordinates of the center M are defined as (0, 0). In a case where the coordinate system is defined in this way, when the number X of pixels in the horizontal direction and the number Y of pixels in the vertical direction are both even numbers, the position of the coordinates of the center M is strictly deviated by 0.5 pixel from the center of the imaging element (matching the position of the optical axis of the lens 210), but this deviation is very small and is ignored.

In step S104, the control data acquirer 112 calculates the coordinates (xc, yc) of the middle point O of the feature point a and the feature point 13 as the center coordinates (hereinafter, referred to as "vaginal speculum center coordinates") of the cross section 310 of the vaginal speculum 300 illustrated in FIG. 8 in the coordinate system (x axis, y axis) defined as described above.

Next, the control data acquirer 112 calculates an angle, at which the major axis 501 of the cross section 310 and the y-axis defined as described above intersect, as the angle of the vaginal speculum 300 (orientation and hereinafter, referred to as "vaginal speculum angle θ") from the feature points α and β (step S105). Specifically, as illustrated in FIG. 8, a straight line connecting the feature point α and the feature point β corresponds to the minor axis 502 of the cross section 310, and the major axis 501 is orthogonal to the minor axis 502 and passes through the middle point O calculated in step S104. Therefore, the control data acquirer 112 obtains the major axis 501 based on the coordinates of the feature point α, the feature point β, and the middle point O, and calculates the angle at which the obtained major axis 501 and the y axis intersect as the vaginal speculum angle θ. Since step S103 to step S105 are steps in which various position parameters used as control data are acquired, they are also called control data acquisition steps.

Figure 7:
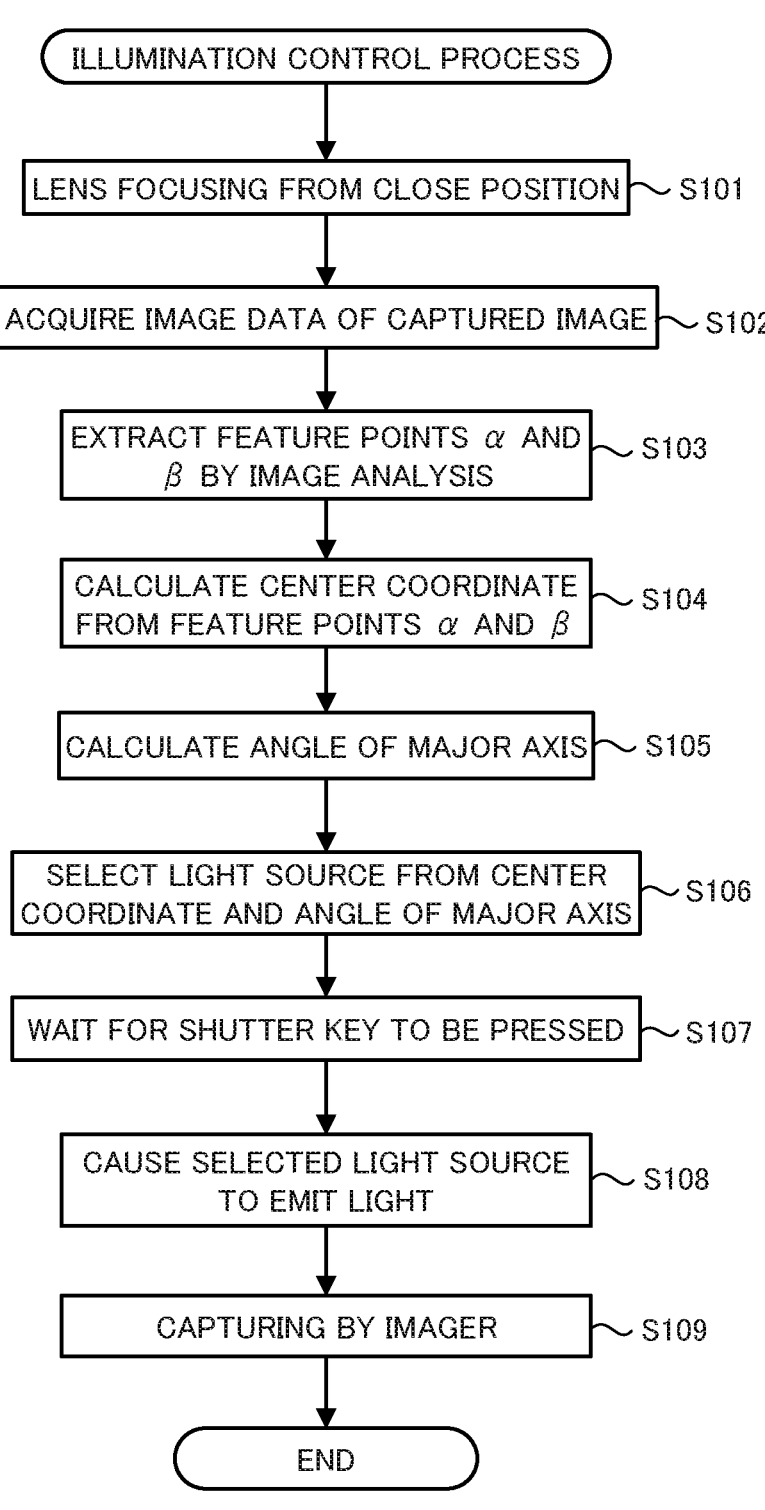
FIG. 7 is a flowchart of an illumination control process according to Embodiment 1.

Although omitted in the flowchart illustrated in FIG. 7, when the illumination control process is started by the user who turns on the focus key 132, a process of turning off the focus key 132 may be performed between step S105 and step S106.

Next, the light source controller 113 selects a target illumination light source for illuminating the cervix 420 (target) from the plurality of light emitters 230a to 230h based on the vaginal speculum center coordinates calculated in step S104 and the vaginal speculum angle θ calculated in step S105 (step S106). Specifically, as shown in FIG. 9, the light source controller 113 sets a range of ±22.5° with respect to an angle, at which a straight line connecting the center M and each of coordinates 221a, 221b, 221c, 221d, 221e, 221f, 221g, and 221h corresponding to the optical axis of each light emitter 230 at the angle of view 221 intersects the y-axis, in correspondence to each light emitter 230, and determines a range within which the vaginal speculum angle θ calculated in step S105 falls among these set ranges. For example, when the vaginal speculum angle θ is 30°, the vaginal speculum angle θ falls within two ranges: a range corresponding to the light emitter 230d and a range corresponding to the light emitter 230h. Then, the light source controller 113 selects a light emitter 230, whose corresponding coordinates 221d and 221h are close to the vaginal speculum center coordinates from these two light emitters 230d and 230h, as a target illumination light source. For example, when the vaginal speculum center coordinates are (xc=−10, yc=100), the light source controller 113 selects the light source 230h as a target illumination light source.

More generally, the light source controller 113 selects a target illumination light source as follows based on the vaginal speculum angle θ and the vaginal speculum center coordinates. When 0°<θ≤22.5° or 157.5°<θ≤180°, the light emitter 230a is selected if yc>0 and the light emitter 230e is selected if yc≤0. When 22.5°<θ≤67.5°, the light emitter 230h is selected if yc>0 and the light emitter 230d is selected if yc≤0. When 67.5°<θ≤112.5°, the light emitter 230 g is selected if xc>0 and the light emitter 230c is selected if xc≤0. When 112.5°<θ≤157.5°, the light emitter 230b is selected if yc>0 and the light emitter 230f is selected if yc≤0.

For the purpose of simplicity, the light source controller 113 makes a determination using either xc or yc out of the two values of the center coordinates xc and yc in each determination, but by making a determination using both the values of xc and yc, a light emitter 230 corresponding to a position closest to the center coordinates (xc, yc) may be selected as a target illumination light source.

Furthermore, the light source controller 113 can also control the illumination state of the light source by using a table in which the relationship between the control data (position parameter) and the illumination state of the light source is defined in advance, without performing the determination process as described above. Examples of this table include a four-dimensional table (θ, xc, yc, and target illumination light source) in which an optimum illumination state (target illumination light source) is defined for values of various position parameters (θ, xc, and yc), a five-dimensional table (x-coordinate and y-coordinate of the feature point α, x-coordinate and y-coordinate of the feature point β, and target illumination light source) in which an optimum illumination state (target illumination light source) is defined for values of various position parameters (x-coordinate and y-coordinate of the feature point α, and x-coordinate and y-coordinate of the feature point β), and the like.

Since the light source controller 113 selects the target illumination light source in this way, when viewed from the vaginal speculum insertion direction, a light emitting part 230, in which a straight line connecting the optical axis of the imaging device 200 and the optical axis of the light emitter 230 matches the major axis 501 of the cross section 310 of the vaginal speculum 300 as much as possible and a distance between the vaginal speculum cross section center line and the optical axis of the light emitting part 230 is as small as possible, that is, a light emitter 230, which can irradiate the widest range of the cervix 420 with light, is selected.

Returning to FIG. 7, the controller 110 then waits for the shutter key 133 to be pressed by the user (step S107). When the shutter key 133 is pressed, the light source controller 113 causes the target illumination light source selected in step S106 to emit light (step S108). Step S106 and step S108 are also referred to as an illumination control step.

Then, the photography controller 114 photographs the cervix 420 together with the vaginal speculum 300 by the imager 220 in a state where the light source controller 113 causes the target illumination light source selected in step S106 to emit light (step S109), and ends the illumination control process.

By the illumination control process described above, the light source controller 113 selects, as a target illumination light source, a light emitter 230 capable of irradiating the widest range of the cervix 420 with light from the plurality of light emitters 230 and causes the selected light emitter 230 to emit light, so that the illumination control device 100 can appropriately illuminate the cervix 420 even though the user adjusts no position.

Furthermore, the light source controller 113 controls the illumination state of the light emitter 230 according to the control rule (step S106 in FIG. 7) constructed based on the relationship between the control data (position parameter) and the illumination state (target illumination light source) of the light source, so that the control rule can be easily corrected even when the illumination state is to be changed.

Furthermore, the control data acquirer 112 acquires, as control data, the position parameter representing the position of the vaginal speculum 300 in the captured image obtained by capturing the vaginal speculum 300 and the cervix 420, thereby controlling the illumination state of the light emitter 230 based on the positional relationship between the vaginal speculum 300 and the light emitter 230 provided around the optical axis of the lens 200.

Furthermore, when the cross section 310 of the vaginal speculum 300 has an elliptical shape, the control data acquirer 112 acquires the center coordinates of the cross section 310 and the vaginal speculum angle θ as position parameters serving as the control data, but these position parameters can be easily acquired by image analysis of the captured image obtained by capturing the vaginal speculum 300.

Furthermore, the light source controller 113 selects the target illumination light source from the plurality of light emitters 230 according to the determination process and the table constructed based on the relationship between the position parameter and the target illumination light source, thereby selecting an optimum target illumination light source without machine learning the relationship between the position parameter and the target illumination light source.

Furthermore, the imaging device 200 can photograph a target such as the cervix 420 appropriately illuminated by the above-mentioned illumination control device 100.

Embodiment 2

In Embodiment 1 described above, any image analysis technique can be used for extracting position parameters (for example, the feature points α and β) used for selecting a target illumination light source. However, the extraction accuracy of the position parameter depends on an image analysis algorithm. On the other hand, when a large amount of image data to which a target illumination light source to be selected is assigned as a correct answer label can be prepared as data for machine learning, for example, by machine learning a convolutional neural network (CNN) using the image data as learning data, a target illumination light source can be appropriately selected without preparing an image analysis algorithm. Such Embodiment 2 is described.

Since the configuration and external appearance of the imaging device 200 according to Embodiment 2 are the same as those of Embodiment 1, description thereof is omitted. However, the control data acquirer 112 according to Embodiment 2 acquires the image data acquired by the image data acquirer 111 as is. Furthermore, the light source controller 113 according to Embodiment 2 includes a CNN. The CNN is a neural network machine-learned by a learning process to be described below so as to output a target state of an illumination state of a light source (for example, a light emitter 230 capable of irradiating the widest range of the cervix 420 with light) when the image data acquired by the image data acquirer 111 is received as control data.

Figure 10:
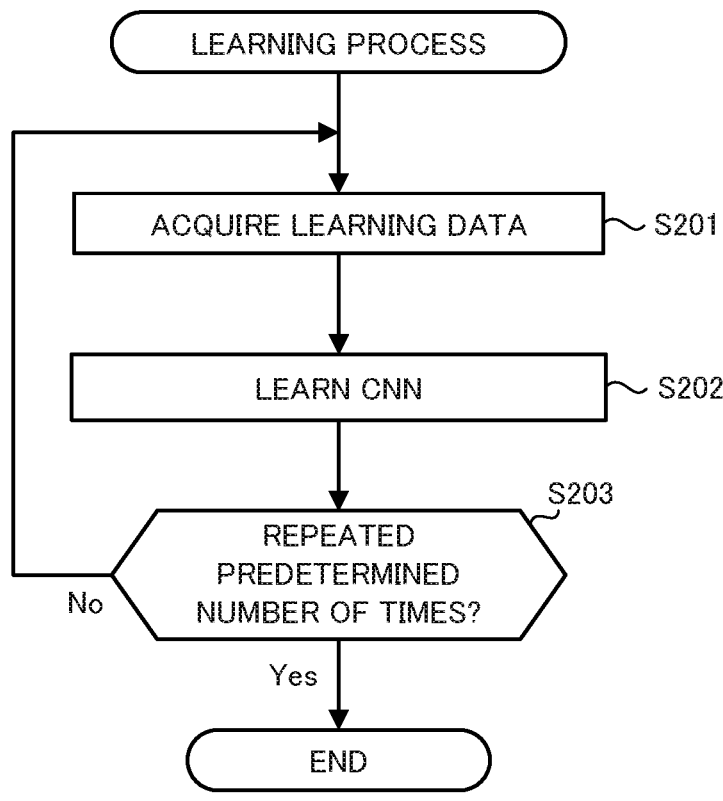
FIG. 10 is a flowchart of a learning process according to Embodiment 2.

The learning process for learning this CNN is described with reference to FIG. 10. This process needs to be completed before an illumination control process to be described below is performed. Furthermore, it is assumed that a learning data set is prepared in advance as data for machine learning, the learning data set being a collection of a large amount of data (learning data) in which a target illumination light source (any of the light emitters 230a to 230h) to emit light is assigned as a correct answer label to the image data of the image obtained by photographing the cervix 420 together with the vaginal speculum 300, the target illumination light source being determined based on the positional relationship between the vaginal speculum 300 and the imaging device 200 when the image is captured. This correct label is assigned to each image data by experiments and simulations.

First, the controller 110 acquires learning data from the learning data set (step S201). Then, the CNN is learned with the acquired learning data (step S202). Specifically, a weighting factor in the CNN is updated by a back propagation method so that a value output from the CNN when the image data included in the acquired learning data is input to the CNN approaches a value (any of the light emitters 230a to 230h) of the correct answer label assigned to the image data.

Next, the controller 110 determines whether or not the processes of step S201 and step S202 have been repeated a predetermined number of times (step S203). The predetermined number of times is, for example, the number of times corresponding to the number of learning data included in the learning data set. When the processes have not been repeated the predetermined number of times (step S203; No), the controller 110 returns the process to step S201. When the processes have been repeated the predetermined number of times (step S203; Yes), the controller 110 ends the learning process.

Figure 11:
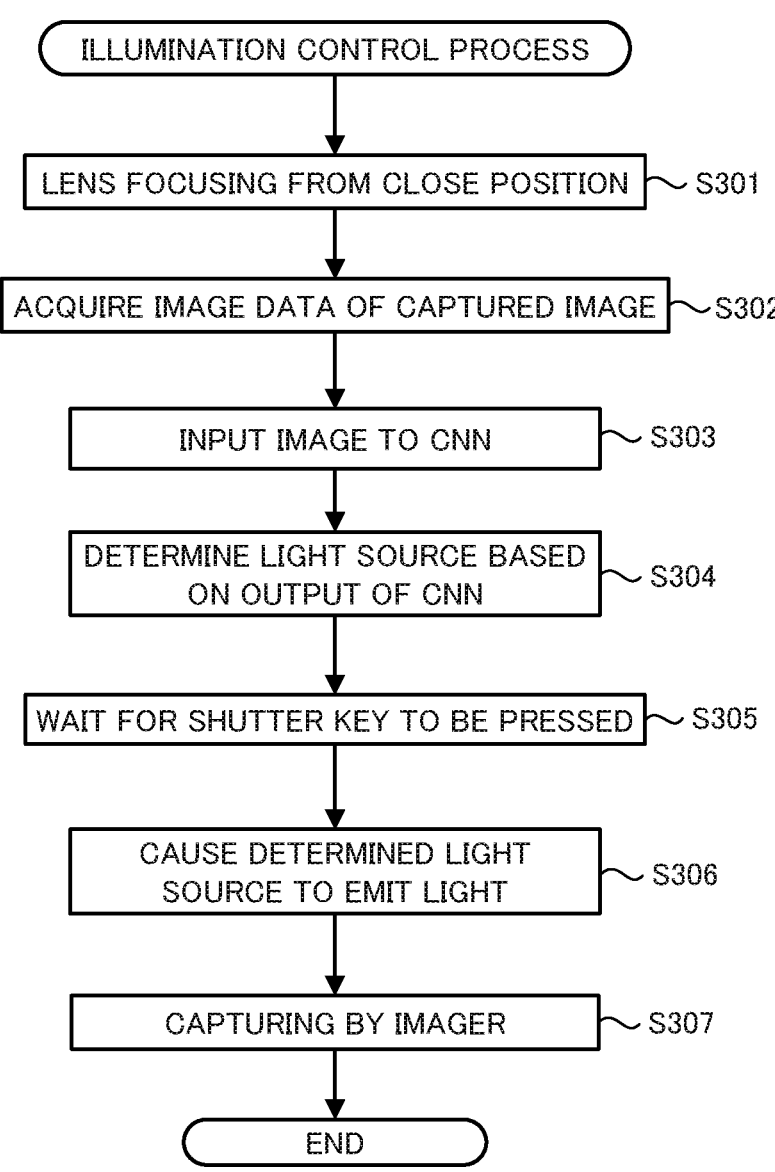
FIG. 11 is a flowchart of an illumination control process according to Embodiment 2.

Next, the illumination control process using the CNN learned by the above learning process is described with reference to FIG. 11. This process starts when an instruction to start the illumination control process is received from the user via the operator 130, but for example, when the user turns on the focus key 132, the lighting control process is started.

First, the image data acquirer 111 changes the focal length or the extension amount of the lens 210 in order to find a focus distance that is in focus from the closest distance toward infinity, and searches for a focus distance to be focused first (step S301). Then, the image data acquirer 111 acquires image data of a captured image (live view image) captured by the imager 220 through the focused lens 210 (step S302).

Next, the control data acquirer 112 inputs the image data acquired in step S302 to the CNN of the light source controller 113 as control data (step S303). Then, based on a value output from the CNN and representing the light emitter 230, the light source controller 113 determines any of the light emitters 230a to 230h as a target illumination light source to emit light (step S304). Then, the controller 110 waits for the shutter key 133 to be pressed by the user (step S305). When the shutter key 133 is pressed, the light source controller 113 causes the target illumination light source determined in step S304 to emit light (step S306).

Then, the photography controller 114 photographs the cervix 420 together with the vaginal speculum 300 by the imager 220 in a state where the light source controller 113 causes the target illumination light source determined in step S304 to emit light (step S307), and ends the illumination control process.

The illumination control device 100 according to Embodiment 2 can use a neural network in which the relationship between the control data reflecting the position parameter and the illumination state of the light source (target illumination light source) is machine-learned with a large amount of learning data, and appropriately illuminate the cervix 420 without generating, for example, an image analysis algorithm for extracting the above-mentioned feature points α and β. Although the CNN has been described as an example of a model for machine learning, a support vector machine (SVM), a decision tree, or the like may be machine-learned and used instead of the CNN.

Modification of Embodiment 2

In above described Embodiment 2, data, in which a target illumination light source (any of the light emitters 230a to 230h) is assigned as a correct answer label to the image data of the image obtained by capturing the cervix 420 together with the vaginal speculum 300, is used as learning data for machine learning the CNN, the target illumination light source being determined based on the positional relationship between the vaginal speculum 300 and the imaging device 200 when the image is captured. However, the method of selecting the target illumination light source by machine learning is not limited to thereto.

For example, as the learning data, two types of learning data are prepared: first learning data for outputting the feature points α and β from the image data and second learning data for outputting an optimum light emitter 230 from the feature points α and β, and the target illumination light source may be selected using a CNN learned by the first learning data and a neural network learned by the second learning data. In such a case, the first learning data uses data in which the coordinates of each of the feature points α and β in the image obtained by photographing the vaginal speculum 300 together with the cervix are assigned to the image data of the image as correct answer labels. The second learning data uses data in which an optimum target illumination light source (any of the light emitters 230a to 230h) in the case of the coordinates of the feature points α and β is assigned as a correct answer label to the set of the coordinates of the feature point α and the coordinates of the feature point β.

Furthermore, after obtaining the coordinates of each of the feature points α and β by using the CNN learned using the above-mentioned first learning data, the target illumination light source may also be selected by the same processes as those after step S104 in Embodiment 1. In such a case, step S103 of the illumination control process (FIG. 7) according to Embodiment 1 may be performed by the CNN, and other processes may be performed in the same manner as in Embodiment 1.

The above-mentioned first learning data and second learning data are only examples. For example, after data for outputting the vaginal speculum center coordinates (xc, yc) and the vaginal speculum angle θ from the image data is prepared as the first learning data and learning data for outputting an optimum light emitter 230 from the vaginal speculum center coordinates (xc, yc) and the vaginal speculum angle θ is prepared as the second learning data, the same process may also be performed.

Embodiment 3

The illumination control device 100 according to Embodiments 1 and 2 described above performs a process of selecting a target illumination light source, which is an optimum light emitter 230, from the light emitters 230 provided around the lens 210, and causing the selected target illumination light source to emit light. However, as illustrated in FIG. 5A, the optical axis (line extending in the illumination direction of light from the light emitter 230 and passing through the center of an illumination region of the light and the optical axis 504 in the case of the light emitter 230a) of the light emitter 230 according to embodiments 1 and 2 is fixed in parallel to the optical axis 503 of the lens 210. Therefore, light on the optical axis 504 of the light emitter 230a, which is considered to be the brightest of the light of the light emitter 230a and light in the vicinity thereof are not emitted to the cervix 420. In this regard, Embodiment 3, in which the illumination direction of each light emitter 230 is changed and the optical axis thereof is brought closer to the cervix 420 to irradiate the cervix 420 with brighter light from the light emitter 230, is described.

Figure 12:
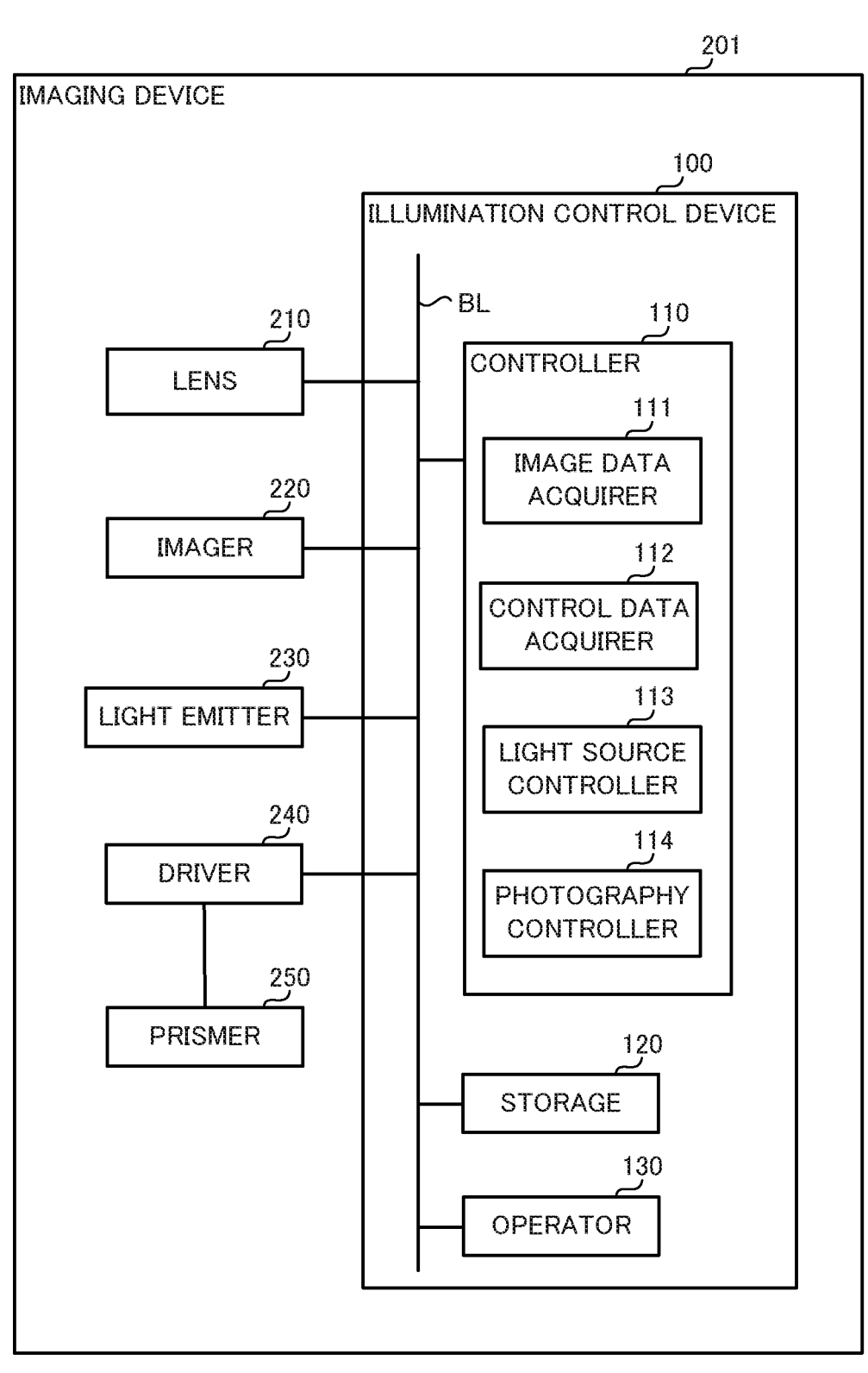
FIG. 12 is a diagram illustrating a functional configuration example of an imaging device according to Embodiment 3.

As illustrated in FIG. 12, an imaging device 201 according to Embodiment 3 has a configuration in which a driver 240 and a prismer 250 are added to the imaging device 200 according to Embodiment 1. As described below, the light emitter 230 and the prismer 250 form a light source in which the illumination direction of light can be changed.

However, the functions of the control data acquirer 112 and the light source controller 113 according to Embodiment 3 are different from those according to Embodiments 1 and 2. These are described below.

The driver 240 includes a stepping motor, and rotates the prismer 250 by an angle instructed by the light source controller 113.

Figures 13A, 13B, 13C, 13D, 13E, 13F:
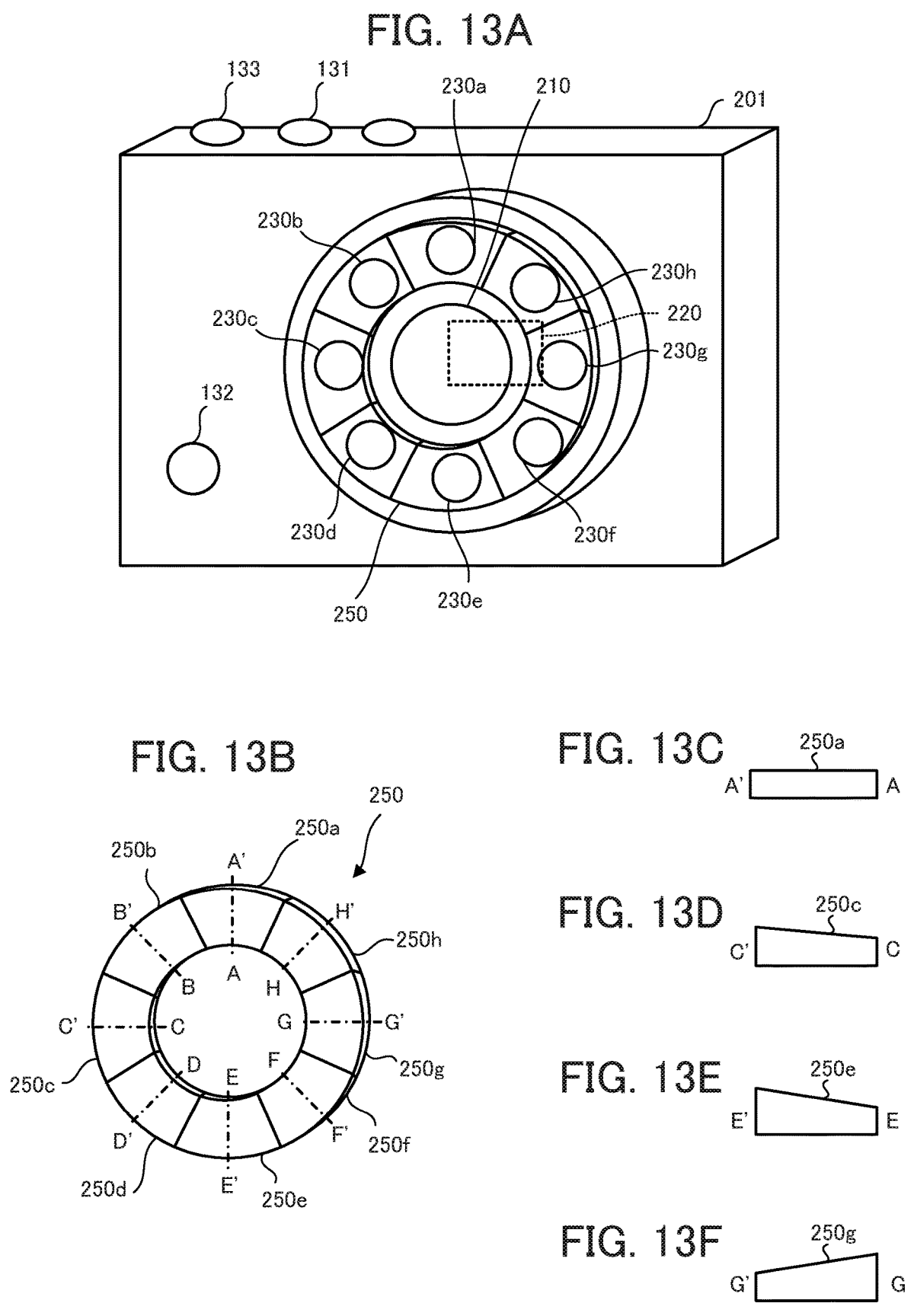

As illustrated in FIG. 13A, the prismer 250 is installed between the light emitter 230 and a target to be photographed of the imaging device 200. Furthermore, as illustrated in FIG. 13B, the prismer 250 has a structure in which a plurality of prisms having different angles formed by an incident surface and an emission surface of light are coupled in a ring shape, and the plurality of prisms are provided in the same number as the plurality of light emitters 230a to 230h. However, as described below, the number of light emitters 230 and the number of prisms do not necessarily have to be the same. Furthermore, the prismer 250 can be rotated about the optical axis of the lens 210 by the driver 240.

FIG. 13C illustrates a cross-sectional view of a prism 250a of the prismer 250 illustrated in FIG. 13B taken along one-dot chain line A-N. In the prism 250a, since an angle formed by an incident surface and an emission surface of light is 0, light from a corresponding light emitter 230 is not refracted by the prism 250a, and its optical axis is parallel to the optical axis of the lens 210 as in the case of Embodiment 1. An angle formed by an incident surface and an emission surface of light in a prism 250b is 0 as in the prism 250a.

FIG. 13D illustrates a cross-sectional view of a prism 250c of the prismer 250 illustrated in FIG. 13B taken along one-dot chain line C-C. In the prism 250c, since an angle formed by an incident surface and an emission surface of light is a relatively small angle S (for example, 5°) in the direction approaching the optical axis of the lens 210, an optical axis from a corresponding light emitter 230 approaches the optical axis of the lens 210 at the angle S when passing through the prism 250c. In a prism 250d, an angle formed by an incident surface and an emission surface of light is S in the direction approaching the optical axis of the lens 210, similarly to the prism 250c.

FIG. 13E illustrates a cross-sectional view of a prism 250e of the prismer 250 illustrated in FIG. 13B taken along one-dot chain line E-E. In the prism 250e, since an angle formed by an incident surface and an emission surface of light is an angle T (for example, 10°) in the direction approaching the optical axis of the lens 210, an optical axis from a corresponding light emitter 230 approaches the optical axis of the lens 210 at the angle T when passing through the prism 250e. In a prism 250f, an angle formed by an incident surface and an emission surface of light is T in the direction approaching the optical axis of the lens 210, similarly to the prism 250e.

FIG. 13F illustrates a cross-sectional view of a prism 250g of the prismer 250 illustrated in FIG. 13B taken along one-dot chain line G-G'. In the prism 250g, since an angle formed by an incident surface and an emission surface of light is an angle U (for example, 10°) in the direction away from the optical axis of the lens 210, an optical axis from a corresponding light emitter 230 separates from the optical axis of the lens 210 at the angle U when passing through the prism 250g. In a prism 250h, an angle formed by an incident surface and an emission surface of light is U in the direction away from the optical axis of the lens 210, similarly to the prism 250g.

In FIG. 13A and FIG. 13B, the prismer 250 is divided into eight regions, but in adjacent regions such as the prism 250a and the prism 250b, since the prisms have the same refraction angle (refractive index), the prisms have four types of selectable refraction angles as a whole. This is because, as described below (as another modification), the same refraction angle can be set when the plurality of light emitters 230 adjacent to each other are made to emit light.

Furthermore, the above-mentioned prismer 250 is only an example, and the prismer 250 is not limited to such a structure. The number of regions of the prismer 250 can be arbitrarily set according to the number of types of refraction angles to be set. Moreover, the prismer 250 may be a prism whose angle changes steplessly from one angle (for example, —20° inward (for example, 20° outward)) to the other angle (for example, 20° inward).

Furthermore, when there is a mode in which light emitters 230 facing each other (for example, the light emitter 230a and the light emitter 230e) are simultaneously made to emit light instead of adjacent light emitters 230, prisms facing each other (for example, the prism 250a and the prism 250e) may be set to have the same refraction angle.

Figure 14A:
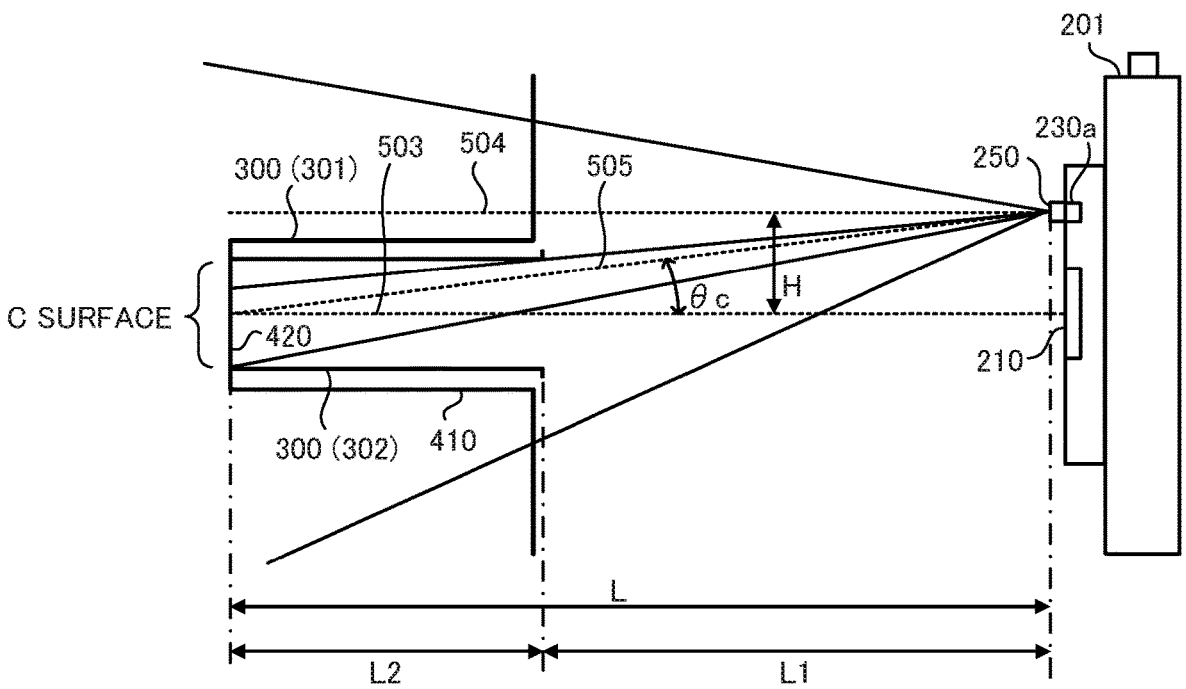
FIG. 14A is a diagram for explaining a light illumination state when the cervix is captured through the vaginal speculum by the imaging device according to Embodiment 3.
Figure 14B:
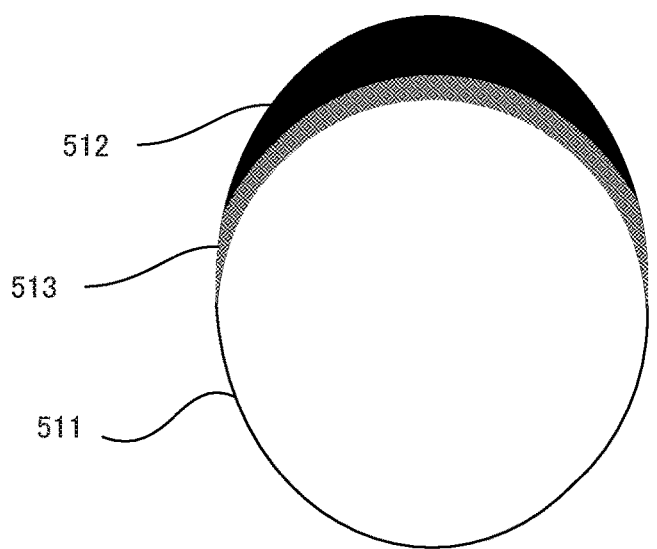
FIG. 14B is a view for explaining an example of a light illumination state on the surface of the cervix.

In the imaging device 201 according to Embodiment 3, as illustrated in FIG. 14A, an optical axis 505 of light having passed from the light emitter 230a to the prismer 250 is refracted by the prism 250b or the prism 250c of the prismer 250 toward the vaginal speculum cross section center line matching the optical axis of the vaginal speculum 200 when viewed in the vaginal speculum insertion direction, and can reach the cervix 420. In such a case, as illustrated in FIG. 14B, on the surface (C surface) of the cervix 420, between a region 511 where light from the light emitter 230a reaches and a shadow region 512 (vignetting) where no light reaches, a region 513 where a boundary between the two regions is blurred is formed. Compared to FIG. 5C and FIG. 14B, an area of the area 511 where light reaches does not change. A portion of the region 512 in FIG. 5C corresponding to a portion close to the region 511 is the region 513 with a blurred boundary in FIG. 14B, and the shadow region 512 in FIG. 14B has a smaller area than the shadow region 512 in FIG. 5C.

It is considered that the shaded region 513 is formed at an edge of the shadow area 512 in the case of FIG. 14B because the brightness of light emitted to the region 511 is higher in the case of FIG. 14B than in the case of FIG. 5C. That is, by aligning the optical axis 505 of the light emitter 230 refracted by the prismer 250 with the surface (C surface) of the cervix 420 as illustrated in FIG. 14A, not only the surface (C surface) of the cervix 420 can be brightly illuminated, but also the area of the shadow region 512 can be reduced.

In order to align the optical axis 505 of light having passed from the light emitter 230 to the prismer 250 with the center of the surface (C surface) of the cervix 420, a refraction angle of the optical axis of the light emitter 230 by the prismer 250 may be set to an angle θc expressed by equation (3) below as illustrated in FIG. 14A.

$$\theta c = \arctan(H/L) \tag{3}$$

In equation (3) above, a distance H is the shortest distance from the optical axis 503 of the lens 210 to the optical axis of each light emitter 230 (optical axis 504 before prism transmission) when the light is not refracted by the prismer 250, and a distance L is the shortest distance from a position where a light emission surface of the prismer 250 is projected perpendicularly to the optical axis 503 of the lens 210 to the surface of the cervix 420. The distance L is the sum of a distance L1 from the position where the light emission surface of the prismer 250 is projected perpendicularly to the optical axis 503 of the lens 210 to the entrance of the vaginal speculum 300, and a length L2 of the vaginal speculum 300.

Since the functions of the control data acquirer 112 and the light source controller 113 according to Embodiment 3 are different from those according to embodiments 1 and 2, these are described. The control data acquirer 112 according to Embodiment 3 acquires the distance L from the imaging device 201 to the cervix and the distance H from the optical axis of the lens 210 to the light emitter 230 as control data. The distance L and the distance H are positional parameters representing the positional relationship between the light emitter 230 and the vaginal speculum 300.

As described below, the control data acquirer 112 acquires the distance L1 from the center of the lens 210 to the entrance of the vaginal speculum 300 in order to acquire the distance L, but the distance L1 corresponds to a focus distance (when focused on the entrance of the vaginal speculum 300) when an image of the cervix 420 is captured by the imager 220 together with the vaginal speculum 300. That is, since the distance L1 is data related to this imaging (target imaging-related data), the control data acquirer 112 serves as data acquisition means for acquiring the target imaging-related data when acquiring the distance L1.

Furthermore, the light source controller 113 according to Embodiment 3 calculates the optimum angle θc of the optical axis of the light emitter 230 with respect to the optical axis 503 based on the distance L and the distance H acquired by the control data acquirer 112, rotates the prismer 250 by controlling the driver 240, and moves a prism that refracts the optical axis of a light emitter 230 to emit light by the angle θc in front of the light emitter 230. By rotating the prismer 250 in this way, the light source controller 113 controls the illumination direction of the light source as the illumination state of the light source.

Figure 15:
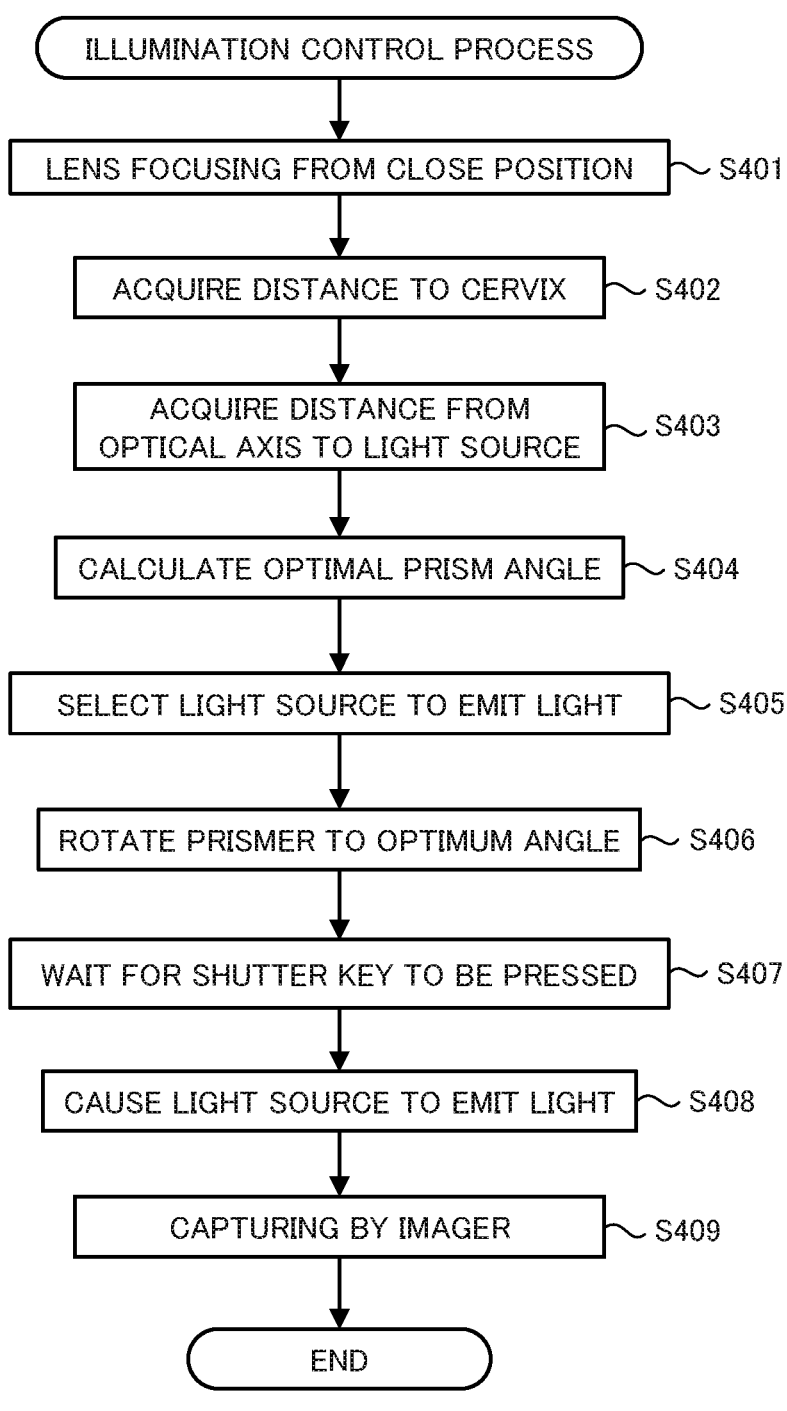
FIG. 15 is a flowchart of an illumination control process according to Embodiment 3.

An illumination control process for controlling the illumination direction of light of the light emitter 230 by using the prismer 250 as described above in order to illuminate the surface of the cervix 420 as brightly as possible is described with reference to FIG. 15. The start condition of this process is the same as that of the illumination control process of FIG. 7. Furthermore, since the distance H from the optical axis 503 of the lens 210 to the center of the light emitter 230 and the length L2 of the vaginal speculum 300 are stored in the storage 120 in advance or input from the operator 130 in advance, the distance H and the length L2 are assumed to be stored in the storage 120 when the illumination control process is started.

First, the image data acquirer 111 changes the focal length or the extension amount of the lens 210 in order to find a focus distance that is in focus from the closest distance toward infinity, and searches for a focus distance to be focused first (step S401).

Next, the control data acquirer 112 obtains the distance L1 from the center of the lens 210 to the entrance of the vaginal speculum 300 based on the focal length or the extension amount of the focused lens 210 (specifically, the distance L1=focus distance and the focus distance is obtained by equation (2) above), and acquires the distance L to the cervix 420 by adding the length L2 of the vaginal speculum 300 stored in the storage 120 to L1 (step S402). The calculation of the distance L1 by equation (2) above and the calculation of the distance L by L1+L2 are only examples of a calculation method. The control data acquirer 112 may obtain the distance L1 or the distance L by another appropriate method, or may obtain the distance L without obtaining the distance L1.

Then, the control data acquirer 112 acquires the distance H from the optical axis of the lens 210 to the light emitter 230 from the storage 120 (step S403). Next, the light source controller 113 calculates the angle θc, which is the optimum refraction angle by the prismer 250, by equation (3) above (step S404).

Next, the light source controller 113 selects a light emitter 230 (any of the light emitters 230a to 230h) to emit light (step S405). The light emitter 230 to emit light is assumed to be selected via the operator 130 (any one of the light emitters 230a to 230h), unlike embodiments 1 and 2.

Then, based on the angle θc calculated in step S404 and the light emitter 230 selected in step S405, the light source controller 113 rotates the prismer 250 by the driver 240 so that a prism having an optimum refraction angle (refractive index) among the plurality of prisms 250a to 250h of the prismer 250 overlaps the light emitter 230 selected in step S405 (step S406). When rotating the prismer 250 by the driver 240 to a reference angle (for example, an angle at which the prism 250a overlaps the light emitter 230a), the light source controller 113 ascertains in advance which of the light emitters 230a to 230h with which each of the prisms 250a to 250h is overlapped, and controls a rotation angle with respect to the reference angle in step S406 so that the selected light emitter 230 overlaps the prism having the optimum refraction angle.

Then, the controller 110 waits for the shutter key 133 to be pressed by the user (step S407). When the shutter key 133 is pressed, the light source controller 113 causes the light emitter 230 selected in step S405 to emit light (step S408).

Then, the photography controller 114 photographs the cervix together with the vaginal speculum 300 by the imager 220 in a state where the light source controller 113 causes the light emitter 230 selected in step S405 to emit light (step S409), and ends the illumination control process.

By the illumination control process described above, based on on the positional relationship between the light emitter 230 and the vaginal speculum 300 based on a focus distance (target imaging-related data related to target imaging) when an image of the cervix (target) is captured by the imaging device 200, since light from the light emitter 230 is refracted by the prismer 250 so that its optical axis matches the center of the cervix, the illumination control device 100 can appropriately illuminate the cervix 420 even though the user adjusts no position.

As the value of H, the shortest distance from the vaginal speculum cross section center line described above to the optical axis 504 of the light emitter 230 selected in step S405 before prism transmission may be used.

Furthermore, when the refraction angle of the prism of the prismer 250 is further subdivided (or stepless), the following processing may be performed between step S406 and step S407. That is, first, light from the light emitter 230 (light source) is emitted to the vaginal speculum 300 (inserter) and the cervix (target) through a first prism selected from the prisms 250a to 250h of the prismer 250. Next, an image of the cervix is captured together with the vaginal speculum 300 in the state where the light from the light emitter 230 is emitted to the vaginal speculum 300 and the cervix through the first prism as described above, and image data acquired by the capturing is used as first captured image data. Next, a second prism having a refractive index of light different from that of the first prism is selected from the prisms 250a to 250h, and the target is irradiated with the light through the selected second prism. Next, an image of the target is captured together with the vaginal speculum 300 in the state where the light from the light emitter 230 is emitted to the target through the second prism as described above, and image data acquired by the capturing is used as second captured image data By performing the same process on a third prism of the prisms 250a to 250h, which is different from the first and second prisms, third captured image data is acquired. Next, the first to third image data are image-analyzed. Next, based on analysis results of the first to third image data, a prism corresponding to more optimal (bright or less vignetting) image data among the first to third image data is specified from the first to third prisms. The prismer 250 may be rotated to an optimum angle so that light from the light emitter 230 is emitted through the specified prism.

Modification of Embodiment 3

In above described Embodiment 3, a light emitter 230 to emit light is a light emitter 230 selected by the user via the operator 130, but is not limited thereto. For example, the light emitter 230 to emit light may be selected in the same manner as in Embodiment 1 or 2. The modification of Embodiment 3 is described.

Figure 16:
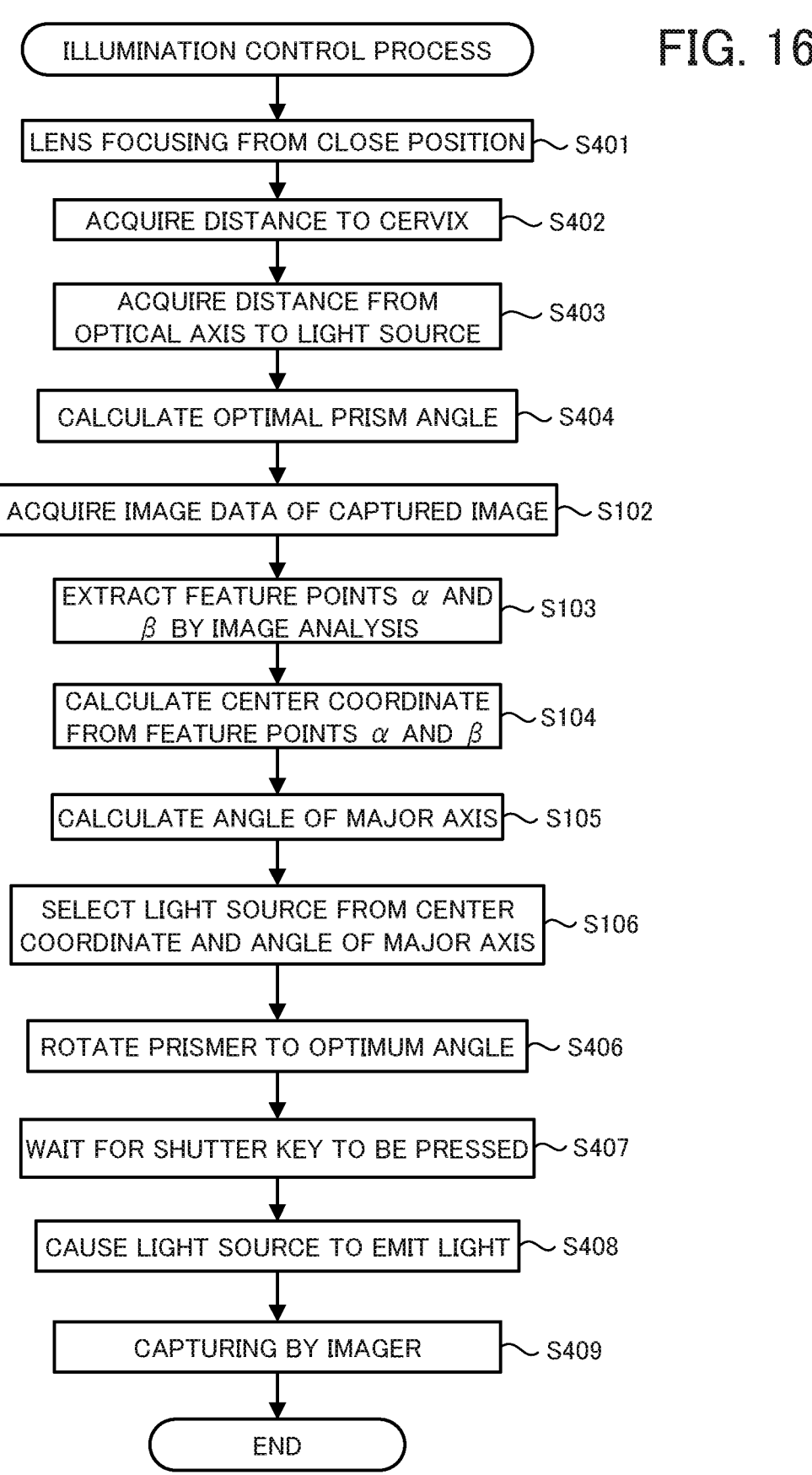
FIG. 16 is a flowchart of an illumination control process according to a modification of Embodiment 3.

Since the configuration and external appearance of the imaging device 201 according to the modification of Embodiment 3 are the same as those of Embodiment 3, description thereof is omitted. Furthermore, as illustrated in FIG. 16, an illumination control process according to the modification of Embodiment 3 is a process in which step S405 in the illumination control process of Embodiment 3 is replaced with step S102 to step S106 of the illumination control process of Embodiment 1.

That is, the light source controller 113 selects the light emitter 230 in steps S102 to S106 instead of selecting the light emitter 230 in step S405. Furthermore, in step S408, the light source controller 113 causes the light emitter 230 selected in step S106 to emit light.

By the above illumination control process, in the modification of Embodiment 3, a light emitter 230 capable of irradiating the widest range of the cervix 420 with light from the plurality of light emitters 230 is selected as a target illumination light source and emits light, and the light from the target illumination light source is refracted by the prismer 250 so that its optical axis reaches the cervix 420, so that the cervix 420 can be appropriately illuminated by the light even though the user adjusts no position.

Other Modifications

The present disclosure is not limited to the embodiments described above, and various changes can be made. For example, in Embodiment 3, in a case where the optimum refraction angle θc is acquired by the prismer 250, when image data acquired by the image data acquirer 111 is input as control data, a machine-learned CNN may be used to output the optimum refraction angle θc.

Furthermore, the modification of Embodiment 3 described above is an embodiment in which Embodiment 1 and Embodiment 3 are combined, but the same effect can also be obtained in an embodiment in which Embodiment 2 and Embodiment 3 are combined to select the target illumination light source and change the refraction angle θc by the prismer 250.

Furthermore, in the embodiments described above, the light source controller 113 selects one light emitter 230 from the plurality of light emitters 230 and causes the selected light emitter 230 to emit light, but the number of light emitters 230 to emit light is not limited to one. However, it has been experimentally confirmed that when a light emitter 230 located at a remote position is selected as the light emitter 230 to emit light, a range in which an illumination state is good is conversely narrowed.

Figure 17A:
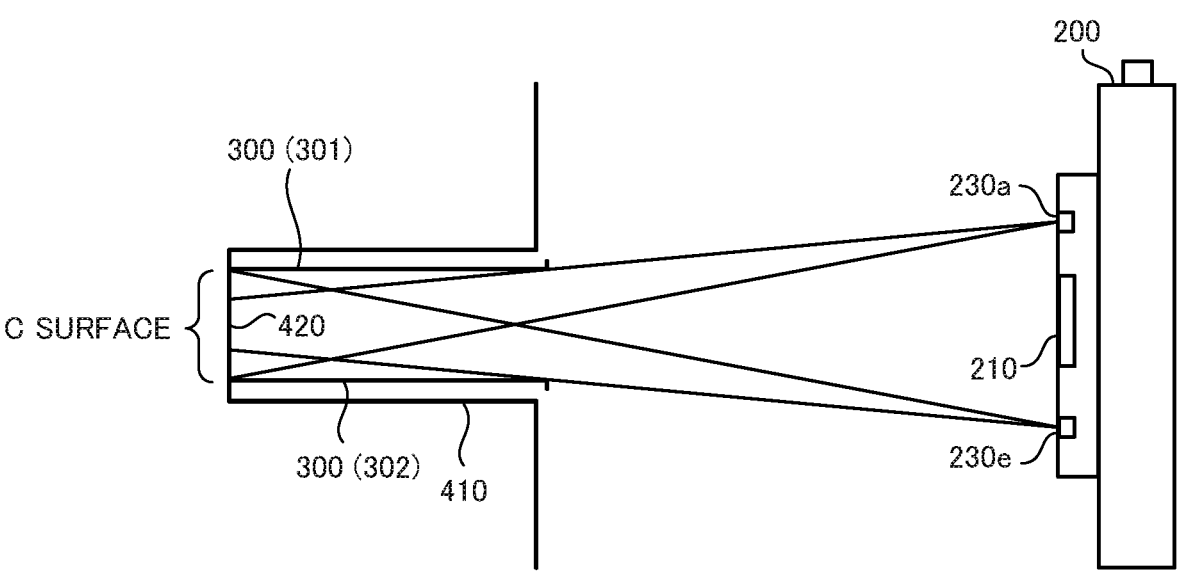
FIG. 17A is a diagram for explaining a light illumination state when light emitters facing each other are made to emit light when viewed from the direction in which an optical axis of the imaging device extends in a case where the cervix is captured through the vaginal speculum by the imaging device.
Figure 17B:
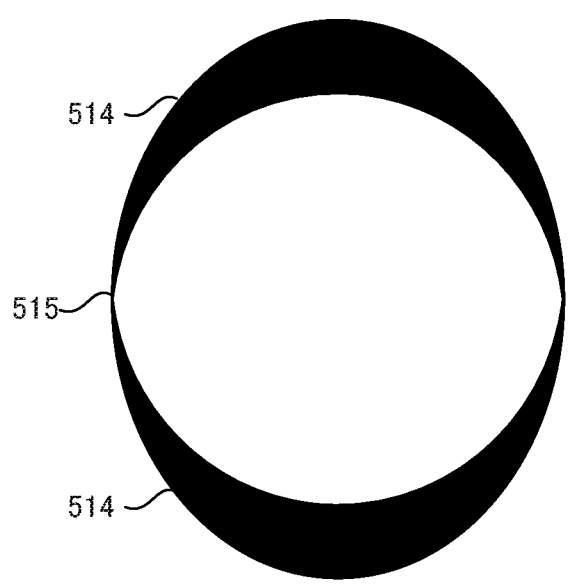
FIG. 17B is a diagram for explaining an example of a light illumination state on the surface of the cervix when the light emitters are made to emit light as illustrated in FIG. 17A.

For example, as illustrated in FIG. 17A, when the light emitter 230a and the light emitter 230e facing each other among the plurality of light emitters 230 are made to emit light when viewed from the direction in which the optical axis of the imaging device 200 extends, the brightness of a central region 515 is twice the brightness of upper and lower regions 514, and the region 514 is observed as a shadow region even though the region 514 is irradiated with light from one light emitter 230, as illustrated in FIG. 17B. Therefore, an area of the region 515, where the illumination state is good, is reduced compared to a case where only one light emitter 230 is made to emit light.

Accordingly, when a plurality of light emitters 230 are selected to emit light, it is desirable that light emitters 230 close to each other (for example, the light emitter 230a and the light emitter 230b adjacent to each other, and the like) are made to emit light. As long as the plurality of light emitters 230 are close to each other, even though the plurality of light emitters 230 are made to emit light, an illumination state similar to the illumination state illustrated in FIG. 14B is obtained. For example, the light source controller 113 may select a total of three light emitters 230, that is, a light emitter 230 capable of irradiating the widest range of the cervix 420 with light and light emitters 230 on both sides of the light emitter 230, from the plurality of light emitters 230, and cause the three light emitters 230 to emit light.

In the embodiments described above, image data acquired by the image data acquirer 111, which is used by the control data acquirer 112 to acquire control data, is image data captured without causing the light emitter 230 to emit light, but is not limited thereto and may be image data captured by causing the light emitter 230 to emit light. Furthermore, when the light emitter 230 is made to emit light, it is arbitrary which light emitter 230 is selected to emit light.

Furthermore, in the embodiments described above, since the light emitters 230 are arranged in a ring shape, the prismer 250 is also provided in a ring shape, but the shape of the prismer 250 is not limited to the ring shape. For example, when the light emitter 230 is a single light source or a plurality of light sources arranged in the left-right direction, the prismer 250 may be a prismer 250 in which a prism through which light from the light emitter 230 passes is changed by sliding in the left-right direction.

Furthermore, the prismer 250 may be a prismer 250 having a refractive index that is changed by stacking or not stacking prisms in the optical axis direction of a camera. Furthermore, the prismer 250 is only an example of means for controlling the illumination direction of a light source. The means for controlling the illumination direction of the light source may include not only a prism but also a mechanism for changing the illumination direction of light from the light source by changing the angle of a mirror provided between the light source and a target, for example, or a mechanism capable of changing the angle of an optical axis of the light source with respect to an optical axis of the camera by driving the light source with an actuator.

Furthermore, in the embodiments described above, the imaging devices 200 and 201 for photographing the human cervix have been described as an example; however, a target to be photographed by the imaging devices 200 and 201 is not limited to the human cervix and may be the cervix of a non-human animal (for example, dog, cat, cow, pig, horse, and the like). Moreover, the target to be photographed by the imaging devices 200 and 201 is not limited to the cervix and the control of the light source by the illumination control device 100 is not limited to a light source that illuminates the cervix. Furthermore, the imaging devices 200 and 201 can also be used for capturing an image in a pipe in a factory or a work site or in a gap where no person enters, or capturing an image in a hole in the natural world (animal burrow, tree hollow, crack or hole in the ground or cliff).

That is, the imaging devices 200 and 201 and the illumination control device 100 can be generally used when inserting an inserter (vaginal speculum, throat mirror, nasal speculum, otoscope, anoscope, sewer pipe mirror, or the like) into a hole part (vagina, oral cavity, nare (entrance of nasal cavity), hole of ear (entrance of ear canal), anus, pipe such as a sewer pipe, or the like), and photographing a target at the back of the hole part (cervix, throat, nasal wall (superior nasal concha, middle nasal concha, and inferior nasal concha), ear canal wall, eardrum, rectum, sewer wall, antrum wall, or the like).

Furthermore, in the embodiments described above, the imaging devices 200 and 201 have been described as having the illumination control device 100 therein; however, the illumination control device 100 may be a device separate from the imaging devices 200 and 201. In such a case, each of the illumination control device 100 and the imaging devices 200 and 201 includes a communicator, and the illumination control device 100 is configured to be able to control the imaging devices 200 and 201 via the communicator.

Each function of the illumination control device 100 can also be performed by a computer such as an ordinary PC. Specifically, in the above embodiments, the program for the illumination control process performed by the illumination control device 100 has been described as being stored in the ROM of the storage 120 in advance. However, a computer capable of implementing each of the above-mentioned functions may be configured by storing the program in a computer-readable recording medium such as a flexible disk, a compact disc read only memory (CD-ROM), a digital versatile disc (DVD), a magneto-optical disc (MO), a memory card, or a universal serial bus (USB) memory, distributing the program, and installing the program by reading the program into the computer.

Although the preferred embodiments of the present disclosure have been described above, the present disclosure is not limited to specific embodiments and includes the invention defined in the appended claims and the equivalent range thereof.

This application claims the benefit of Japanese Patent Application No. 2020-054891, filed on Mar. 25, 2020, the entire disclosure of which is incorporated by reference herein.

INDUSTRIAL APPLICABILITY

The present disclosure is applicable to an illumination control device, an imaging device, an illumination control method, and a program, capable of appropriately illuminating a target to be photographed even though a user adjusts no position.

REFERENCE SIGNS LIST

100 Illumination control device
110 Controller
111 Image data acquirer
112 Control data acquirer
113 Light source controller
114 Photography controller
120 Storage
130 Operator
131 Light emitting release button
132 Focus key
133 Shutter key
200, 201 Imaging device
210 Lens
220 Imager
221 Angle of view
221*a*, 221*b*, 221*c*, 221*d*, 221*e*, 221*f*, 221*g*, 221*h* Coordinate
222 Imaging element
230, 230*a*, 230*b*, 230*c*, 230*d*, 230*e*, 230*f*, 230*g*, 230*h* Light emitter
240 Driver
250 Prismer
250*a*, 250*b*, 250*c*, 250*d*, 250*e*, 250*f*, 250*g*, 250*h* Prism
300 Vaginal speculum
301 Upper part
302 Lower part
303, 303*a*, 303*b* Main part
310 Cross section
410 Vagina
411 Thick wall
420 Cervix
501 Major axis
502 Minor axis
503, 504, 505 Optical axis
511, 512, 513, 514, 515 Region
601 Subject
BL Bus line
D, H, L, L1 Distance
F Focal length
K Extension amount
L2 Length
M Center
O Middle point
$\alpha$, $\beta$ Feature point
$\theta$ Vaginal speculum angle
$\theta c$ Angle

What is claimed is:

1. An illumination control device comprising a hardware processor configured to execute processes comprising:
a data acquisition process of acquiring target imaging-related data related to target imaging, the target imaging-related data being data obtained by performing the target imaging in such a state that an image of an inserter inserted into a hole part continuous with a target is captured by an imaging device together with the target;
a control data acquisition process of acquiring control data based on the target imaging-related data; and
an illumination control process of controlling an illumination state of a light source provided around an optical axis of the imaging device, based on the control data, wherein:
the control data acquisition process includes acquiring, based on the target imaging-related data, a position parameter representing a positional relationship between the light source and the inserter,
the target imaging-related data is image data of a captured image acquired by the target imaging,
a cross section of the inserter orthogonal to an insertion direction into the hole part has a substantially elliptical shape, and
the control data acquisition process includes acquiring, as the position parameter, an angle of a major axis or a minor axis of the cross section of the inserter with respect to a base line extending in a direction orthogonal to the optical axis and a position of a center of the cross section of the inserter with the optical axis of the imaging device in the captured image as a reference.

2. The illumination control device according to claim 1, wherein the illumination control process includes controlling the illumination state of the light source based on the control data according to a control rule constructed based on a relationship between the control data and the illumination state of the light source.

3. The illumination control device according to claim 2, wherein:
the target imaging-related data is image data of a captured image acquired by the target imaging,
the control data acquisition process includes acquiring the control data based on the image data, and
the control rule is a trained neural network having undergone machine-learning with the control data as an input and a target state of the illumination state of the light source as an output.

4. The illumination control device according to claim 1, wherein the illumination control process includes controlling illumination states of a plurality of light sources, selecting a target illumination light source for illuminating the target from the plurality of light sources, and causing the selected target illumination light source to emit light.

5. The illumination control device according to claim 1, wherein:
the light source is configured so that an illumination direction of light of the light source is changeable, and
the illumination control process includes controlling the illumination direction of the light source as the illumination state of the light source.

6. The illumination control device according to claim 1, wherein:
the inserter is a vaginal speculum, and
the target is a cervix.

7. The illumination control device according to claim 1, wherein:
the light source is configured so that an illumination direction of light of the light source is changeable, and
the illumination control process includes controlling the illumination direction of the light source as the illumination state of the light source.

8. An illumination control method, comprising:

acquiring target imaging-related data related to target imaging, the target imaging-related data being data obtained by performing the target imaging in such a state that an image of an inserter inserted into a hole part continuous with a target is captured by an imaging device together with the target;

acquiring control data based on the target imaging-related data; and controlling an illumination state of a light source provided around an optical axis of the imaging device, based on the control data, wherein:

the acquiring the control data includes acquiring, based on the target imaging-related data, a position parameter representing a positional relationship between the light source and the inserter, the target imaging-related data is image data of a captured image acquired by the target imaging, a cross section of the inserter orthogonal to an insertion direction into the hole part has a substantially elliptical shape, and the acquiring the control data includes acquiring, as the position parameter, an angle of a major axis or a minor axis of the cross section of the inserter with respect to a base line extending in a direction orthogonal to the optical axis and a position of a center of the cross section of the inserter with the optical axis of the imaging device in the captured image as a reference.

\*  \*  \*  \*  \*